US007851670B2

(12) United States Patent
Wan et al.

(10) Patent No.: US 7,851,670 B2
(45) Date of Patent: Dec. 14, 2010

(54) METHOD FOR SELECTION OF TRANSFORMED CELLS

(75) Inventors: Yuechun Wan, Madison, WI (US);
Ronald J. Brinker, Ellisville, MO (US);
Paul C. C. Feng, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 428 days.

(21) Appl. No.: 11/758,656

(22) Filed: Jun. 5, 2007

(65) Prior Publication Data
US 2008/0120739 A1 May 22, 2008

Related U.S. Application Data

(60) Provisional application No. 60/811,190, filed on Jun. 6, 2006.

(51) Int. Cl.
C12N 15/82 (2006.01)
C12N 5/04 (2006.01)
A01H 5/00 (2006.01)
C07H 21/04 (2006.01)

(52) U.S. Cl. ............... 800/278; 800/298; 800/300; 800/312; 536/23.2; 536/23.7; 435/415

(58) Field of Classification Search ............... None
See application file for complete search history.

(56) References Cited

U.S. PATENT DOCUMENTS

| | | | |
|---|---|---|---|
| 4,816,403 A | 3/1989 | Roy | 435/253.3 |
| 5,254,799 A * | 10/1993 | De Greve et al. | 800/302 |
| 5,362,865 A | 11/1994 | Austin | 536/24.1 |
| 5,445,962 A | 8/1995 | Atallah et al. | 435/252.1 |
| 5,491,084 A | 2/1996 | Chalfie et al. | 435/189 |
| 5,633,435 A | 5/1997 | Barry et al. | 800/205 |
| 5,656,422 A | 8/1997 | Crawford et al. | 435/4 |
| 5,659,122 A | 8/1997 | Austin | 800/317.3 |
| 5,670,454 A | 9/1997 | Grossmann et al. | 504/244 |
| 5,728,925 A | 3/1998 | Herrera-Estrella et al. | 800/205 |
| 5,850,019 A | 12/1998 | Maiti et al. | 800/205 |
| 6,146,826 A | 11/2000 | Chalfie et al. | 435/6 |
| 6,586,367 B2 | 7/2003 | Lee et al. | 504/127 |
| 7,022,896 B1 * | 4/2006 | Weeks et al. | 800/300 |
| 7,105,724 B2 * | 9/2006 | Weeks et al. | 800/300 |
| 7,230,163 B2 * | 6/2007 | Becton et al. | 800/288 |
| 7,429,691 B2 * | 9/2008 | Zhang et al. | 800/278 |
| 2003/0115626 A1 | 6/2003 | Weeks et al. | 800/300 |
| 2003/0135879 A1 | 7/2003 | Weeks et al. | 800/278 |
| 2004/0097373 A1 | 5/2004 | Lee et al. | 504/128 |
| 2005/0235379 A1 * | 10/2005 | Luo et al. | 800/287 |
| 2006/0235215 A1 * | 10/2006 | Cooper | 536/23.6 |
| 2008/0015110 A1 | 1/2008 | Clemente et al. | 800/300 |
| 2008/0119361 A1 | 5/2008 | Feng et al. | 504/105 |
| 2008/0305952 A1 | 12/2008 | Arnevik et al. | 800/300 |
| 2009/0029861 A1 | 1/2009 | Feng et al. | 800/300 |
| 2009/0081760 A1 | 3/2009 | D'Ordine et al. | 435/189 |
| 2009/0105077 A1 | 4/2009 | Bhatti et al. | 504/206 |

FOREIGN PATENT DOCUMENTS

| | | |
|---|---|---|
| CA | 2165036 | 6/1996 |
| WO | WO 98/45424 | 10/1998 |
| WO | WO 02/068607 | 9/2002 |
| WO | WO 03/034813 | 5/2003 |
| WO | WO 2004/009761 | 1/2004 |
| WO | WO 2005/107437 | 11/2005 |
| WO | WO 2007/143690 | 12/2007 |
| WO | WO 2007/146706 | 12/2007 |
| WO | WO 2008/048964 | 4/2008 |
| WO | WO 2008/051633 | 5/2008 |
| WO | WO 2008/105890 | 9/2008 |

OTHER PUBLICATIONS

Herman et al., "A three-component dicamba O-demethylase from *Pseudomonas maltophilia*, Strain Di-6," *J. of Biological Chemistry*, 280(26):24759-24767, 2005.
Bevan, "Structure and transcription of the nopaline synthase gene region of T-DNA," *Nucleic Acids Res.*, 11(2):369-385, 1983.
Carrington et al. "Cap-independent enhancement of translation by a plant potyvirus 5' nontranslated region," *J. of Virology*, 4:1590-1597, 1990.
Comai et al., "Expression in plants of a mutant aroA gene from *Salmonella typhimurium* confers tolerance to glyphosate," *Nature*, 317:741-744, 1985.
Cork and Krueger, "Microbial Tranformations of Herbicides and Pesticides," *Adv. Appl. Microbiology*, 36:1-67, 1991.
Cork et al., "Detection, isolation, and stability of megaplasmid-encoded chloroaromatic herbicide-degrading genes within *Pseudomonas* species," *Adv. Appl. Microbiol.*, 40:289-321, 1995.
Coruzzi et al., "Tissue-specific and light-regulated expression of pea nuclear gene encoding the small subunit of ribulose-1,5-bisphosphate carboxylase," *EMBO J.*, :(8):1671-1679, 1984.
De Block et al., "Engineering herbicide resistance in plants by expression of a detoxifying enzyme," *EMBO J.*, 6:2513-2518, 1987.
Depicker et al., "Nopaline synthase: transcript mapping and DNA sequence," *J. Mol. Appl. Genet.*, 1:561-573, 1982.
Eckes et al., "Isolation and characterization of a light-inducible, organ-specific gene from potato and analysis of its expression after tagging and transfer into tobacco and potato shoots," *Mol. Gen. Genet.*, 205:14-22, 1986.
GenBank Accession No. E01312, Nov. 4, 2005.
GenBank Accession No. V00087, Mar. 18, 1996.

(Continued)

*Primary Examiner*—Eileen B O Hara
(74) *Attorney, Agent, or Firm*—Pamela J. Sisson; SNR Denton US LLP

(57) ABSTRACT

The invention provides methods for the selection of transgenic cells. The invention relates to the unexpected finding that cells expressing a gene conferring tolerance to auxin-like herbicides such as dicamba may be directly selected from non-transgenic cells using auxin-like herbicides as a selective agent. In this manner, plants exhibiting tolerance to auxin-like herbicides can be directly produced without the need for separate selectable markers.

13 Claims, 9 Drawing Sheets

OTHER PUBLICATIONS

Klee et al.I, "Cloning of an *Arabidopsis thaliana* gene encoding 5-enolpyruvylshikimate-3-phosphate synthase: sequence analysis and manipulation to obtain glyphosate-tolerant plants," *Mol. Gen. Genet.*, 210:437-442, 1987.
Krueger et al., "Isolation and identification of microorganisms for the degradation of dicamba," *J. Agric. Food Chem.*, 37:534, 1989.
Stalker et al., "Herbicide resistance in transgenic plants expressing a bacterial detoxification gene," *Science*, 242:419-423, 1988.
Streber et al., "Transgenic tobacco plants expressing a bacterial detoxifying enzyme are resistant to 2,4-D," *Bio/Technology*, 7:811, 1989.
Khalil et al., "Plasmid-mediated catabolism of dicamba by *Pseudomonas* species strain PXM," *Microbios*, 102:183-191, 2000.
Spencer et al., "Segregation of transgenes in maize," *Plant Molecular Biology*, 18:201-210, 1992.
Weeks et al., "Characterization of a bacterial system capable of degrading dicamba and evaluation of its potential in the development of herbicide-tolerant crops," *J. of Cellular Biochemistry*, Supplement 18A:91, 1994.
"Banvel Herbicide," In: Crop Protection Reference, 11$^{th}$ Edition, pp. 1803-1821, 1995.
Al-Khatib et al., "Foliar absorption and translocation of dicamba from aqueous solution and dicamba-treated soil deposits," *Weed Technology*, 6:57-61, 1992.
U.S. Appl. No. 12/440,173, filed Mar. 5, 2009, Bhatti et al.
Baker, "Response of cotton (*Gossypium hirsutum*) to preplant-applied hormone-type herbicides," *Weed Technology*, 7:150-153, 1993.
Batie et al., "Phthalate dioxygenase reductase and related flavin-iron-sulfur containing electron transferases," In: Chemistry and Biochemistry of Flavoproteins, Muller (Ed.), CRC Press, Boca Raton, FL, pp. 543-556, 1992.
Batie et al., "Purification and characterization of phthalate oxygenase and phthalate oxygenase reductase from *Pseudomonas cepacia*," *J. of Bio. Chem.*, 262(4):1510-1518, 1987.
Bernhardt et al., "A 4-methoxybenzoate O-demethylase from *Pseudomonas putida*. A new type of monoxygenase system," *Eur. J. Biochem.*, 57(1):241-256, 1975.
Butler et al., "Structure-function analysis of the bacterial aromatic ring-hydroxylating dioxygenases," *Advances in Microbial Physiology*, 38:47-85, 1997.
Dehmel et al., "Cloning, nucleotide sequence and expression of the gene encoding a novel dioxygenase involved in metabolism of carboxydiphenyl ethers in *Pseudomonas pseudoalcaligenes* POB310," *Arch. Microbiol.*, 163:35-41, 1995.
Fogarty et al., "Microbiological degradation of the herbicide dicamba," *J. of Industrial Microbiology*, 14:365-370, 1995.
Fukumori et al., "Purification and characterization of 2,-dichlorophenoxyacetate/α-ketoglutarate dioxygenase," *J. Biol. Chem.*, 268:24311-24317, 1993.
Gibson et al., "Aromatic hydrocarbon dioxygenases in environmental biotechnology," *Current Opinion in Biotechnology*, 11:236-243, 2000.
Gurbiel et al., "Active site structure of Rieske-type prteins: electron nuclear double resonance studies of isotopically labeled phthalate dioxygenase from *Pseudomonas cepacia* and Rieske protein from rhodobacter capsulatus and molecular modeling studies of a Rieske center," *Biochemistry*, 35(24):7834-7845, 1996 (Abstract).
Krueger et al., "Use of dicamba-degrading microorganisms to protect dicamba susceptible plant species," *J. of Agri. and Food Chem.*, 39(5):1000-1003, 1991.
Magnusson et al., "Tolerance of soybean (*Glycine max*) and sunflower (*Helianthus annuus*) to fall-applied dicamba," *Weed Sci.*, 35:846-852, 1987.
Markus et al., "Purification and some properties of component A of the 4-chlorophenylacetate 3,4-dioxygenase from *Pseudomonas* species strain CBS," *J. of Biol. Chem.*, 261(27):12883-12888, 1986.
Mason et al., "The electron-transport proteins of hydroxylating bacterial dioxygenases," *Ann. Rev. of Microbiology*, 46:277-305, 1992.
Peniuk et al., "Physiological investigations into the resistance of a wild mustard (*Sinapis arvensis* L.) biotype to auxinic herbicides," *Weed Research*, 33:431-440, 1993.
Sarpe et al., "Researches on resistance of maize hybrids and inbred lines to the herbicides based on 2,4-D and dicamba," *Fragmenta Herbologica Jugoslavica*, 16(1-2):299-305, 1987.
Schroeder et al., "Soft red winter wheat (*Triticum aestivum*) response to dicamba and dicamba plus 2,4-D," *Weed Technology*, 3:67-71, 1989.
Sprague, "Avoid herbicide spray tank contamination," *IPM News*, ipmnews.msu.edu/fieldcrop/tabid/56, Mar. 24, 2010.
Thompson et al., "Soybean tolerance to early preplant applications of 2,4-D ester, 2,4-D amine, and dicamba," *Weed Technology*, 21:882-885, 2007.
Wang et al., "A three-component enzyme system catalyzes the O demethylation of the herbicide dicamba in *Pseudomonas maltophilia* DI-6," *Applied and Environmental Microbiology*, 63(4):1623-1626, 1997.
Wang, "Characterization of cellular and enzymatic degradation of dicamba by *Pseudomonas maltophilia*, Strain DI-6," Thesis, University of Nebraska, Aug. 1996.
Office Action regarding U.S. Appl. No. 11/758,653 dated Dec. 29, 2009.
Amendment and Response to Office Action regarding U.S. Appl. No. 11/758,653, dated Mar. 29, 2010.
Final Office Action regarding U.S. Appl. No. 11/758,653, dated Jun. 24, 2010.
Amendment and Response to Final Office Action regarding U.S. Appl. No. 11/758,653, dated Aug. 16, 2010.
Office Action regarding U.S. Appl. No. 11/758,657 dated Sep. 2, 2009.
Response to Office Action regarding U.S. Appl. No. 11/758,657 dated Jan. 4, 2010.
Final Office Action regarding U.S. Appl. No. 11/758,657, dated Apr. 14, 2010.
Response to Final Office Action regarding U.S. Appl. No. 11/758,657, dated Jul. 14, 2010.
Office Action regarding U.S. Appl. No. 11/758,659 dated Nov. 24, 2009.
Amendment and Response to Office Action regarding U.S. Appl. No. 11/758,659, dated May 24, 2010.
Notice of Allowance regarding U.S. Appl. No. 11/758,659, dated Aug. 3, 2010.
Office Action regarding U.S. Appl. No. 11/758,660, dated Apr. 28, 2010.
Office Action regarding U.S. Appl. No. 10/330,662 dated Apr. 18, 2006.
Interview Summary regarding U.S. Appl. No. 10/330,662, dated Sep. 13, 2006.
Declaration of Donald P. Weeks regarding U.S. Appl. No. 10/330,662, dated Oct. 18, 2006.
Amendment and Response to Office Action regarding U.S. Appl. No. 10/330,662, dated Oct. 18, 2006.
Final Office Action regarding U.S. Appl. No. 10/330,662, dated Jan. 10, 2007.
Amendment and Response to Office Action regarding U.S. Appl. No. 10/330,662, dated Jul. 9, 2007.
Amendment regarding U.S. Appl. No. 10/330,662, dated Jul. 20, 2007.
Office Action regarding U.S. Appl. No. 10/330,662, dated Sep. 21, 2007.
Declaration of Donald P. Weeks regarding U.S. Appl. No. 10/330,662, dated Feb. 20, 2008.
Amendment and Response to Office Action regarding U.S. Appl. No. 10/330,662, dated Mar. 20, 2008.
Office Action regarding U.S. Appl. No. 10/330,662, dated Jul. 9, 2008.
Amendment and Remarks regarding U.S. Appl. No. 10/330,662, dated Jan. 9, 2009.
Final Office Action regarding U.S. Appl. No. 10/330,662, dated Apr. 24, 2009.
Amendment and Remarks regarding U.S. Appl. No. 10/330,662, dated Sep. 24, 2009.
Office Action regarding U.S. Appl. No. 10/330,662, dated Jan. 11, 2010.

Interview Summary regarding U.S. Appl. No. 10/330,662, dated Mar. 19, 2010.
Amendment and Remarks regarding U.S. Appl. No. 10/330,662, dated May 4, 2010.
Notice of Allowance regarding U.S. Appl. No. 10/330,662, dated Jul. 12, 2010.
Notice of Allowance regarding U.S. Appl. No. 11/758,657, dated Sep. 10, 2010.
Response to Office Action regarding U.S. Appl. No. 11/758,660, dated Sep. 27, 2010.
Notice of Allowance regarding U.S. Appl. No. 11/758,653, dated Oct. 5, 2010.
U.S. Appl. No. 12/875,747, filed Sep. 3, 2010, Weeks et al.

* cited by examiner

US 7,851,670 B2

METHOD FOR SELECTION OF TRANSFORMED CELLS

This application claims the priority of U.S. Provisional Patent Application 60/811,190, filed Jun. 6, 2006, the disclosure of which is incorporated herein by reference in its entirety.

BACKGROUND OF THE INVENTION

1. Field of the Invention

The invention relates generally to the field of plant biotechnology. More specifically, the invention relates to methods for selecting transformed plant cells using auxin-like herbicides as a selective agent.

2. Description of the Related Art

Transgenic crops are currently grown on more than 80.0 million hectares world-wide. Improved traits provided by transgenes have significantly increased productivity and in many instances decreased reliance on herbicides and insecticides that can potentially contaminate the environment. However, for transgenic crops to continue to be competitive in the market place, new value-added traits will be required.

In the production of transgenic plants, a particularly important step is the selection of transgenic cells. This is because only a small percentage of cells are typically transformed in any given transformation protocol. The use of a selectable marker gene allows those cells containing a marker gene to be selected away from those that do not. In attempts to stack multiple transgenes in a single plant, this can become particularly difficult, as multiple selectable marker genes are required. Additionally, while a number of selectable markers have previously been described, many do not confer a trait of any practical agronomic value and thus needlessly complicate regulatory approval. Alternatively, labor intensive steps must be taken to attempt to breed selectable markers out of a given transgenic plant. A selectable marker gene with dual functions of a selectable marker and a trait would thus be especially valuable.

Commonly used selectable marker genes for plant transformation are neomycin phosphotransferase II, isolated from Tn5 and conferring resistance to kanamycin (Fraley et al., 1983) and hygromycin phosphotransferase, which confers resistance to the antibiotic hygromycin (Vanden Elzen et al., 1985). Additional selectable marker genes of bacterial origin that confer resistance to antibiotics include gentamycin acetyl transferase, streptomycin phosphotransferase, aminoglycoside-3'-adenyl transferase, and the bleomycin resistance determinant (Hayford et al., 1988; Jones et al., 1987; Svab et al., 1990; Hille et al., 1986).

Other selectable marker genes for plant transformation not of bacterial origin are available. These genes include, for example, mouse dihydrofolate reductase, plant 5-enolpyruvylshikimate-3-phosphate synthase and plant acetolactate synthase (Eichholtz et al., 1987; Shah et al., 1986; Charest et al., 1990). Among some herbicides that selectable marker genes confer resistance to are glyphosate, glufosinate, or bromoxynil (Comai et al., 1985; Gordon-Kamm et al., 1990; Stalker et al., 1988).

Genes encoding enzymes which inactivate herbicides and other xenophobic compounds have previously been isolated from a variety of prokaryotic and eukaryotic organisms. In some cases, these genes have been genetically engineered for successful expression in plants. Through this approach, plants have been developed which are tolerant to the herbicides 2,4-dichlorophenoxyacetic acid (Streber and Willmitzer, 1989), bromoxynil (Stalker et al., 1988), glyphosate (Comai et al., 1985) and phosphinothricin (De Block et al., 1987). While these plants have proven valuable in a commercial setting, plants tolerant to other herbicides are needed to avoid over reliance on any single herbicide and to increase options for managing difficult to control weed species.

In addition to the foregoing herbicides, there are auxin-like herbicides that mimic or act like natural plant growth regulators called auxins. Auxin-like herbicides appear to affect cell wall plasticity and nucleic acid metabolism, which can lead to uncontrolled cell division and growth. The injury symptoms caused by auxin-like herbicides includes epinastic bending and twisting of stems and petioles, leaf cupping and curling, and abnormal leaf shape and venation.

Dicamba is one example of an auxin-like herbicide and is used as a pre-emergent and post-emergent herbicide for the control of annual and perennial broadleaf weeds and several grassy weeds in corn, sorghum, small grains, pasture, hay, rangeland, sugarcane, asparagus, turf, and grass seed crops (Crop Protection Reference, 1995). Unfortunately, dicamba can injure many commercial crops and dicot plants such as soybeans, cotton, peas, potatoes, sunflowers, and canola are particularly sensitive to the herbicide. Despite this, auxin-like herbicides are very effective in controlling weed growth and thus are an important tool in agriculture. This is underscored by the development of weeds tolerant to other herbicides.

Recently, a gene for dicamba monooxygenase (DMO) was isolated from *Pseudomonas maltophilia* that confers tolerance to dicamba (US Patent Appln. 20030135879). DMO is involved in conversion of herbicidal dicamba (3,6-dichloro-o-anisic acid) to a non-toxic 3,6-dichlorosalicylic acid. This gene provides tolerance to dicamba in plants expressing the DMO gene. However, transformants containing the gene had to date only been selected using a separate selectable marker gene and techniques enabling use of a DMO gene as a direct selectable marker were not described. The need to use a separate selectable marker complicates the production of plants tolerant to auxin-like herbicides by requiring an additional gene on transformation vectors used and also presents regulatory hurdles.

Thus, there is a need in the art for new selectable marker genes and new herbicide tolerance genes. Particularly needed is a method for the selection of cells expressing a gene conferring tolerance to dicamba and other auxin-like herbicides that can be directly selected. A selectable marker gene with the dual function of a marker and a trait would eliminate the costs associated with preparing and tracking of two expression units during the development of a product and would facilitate the production of plants having valuable new traits.

SUMMARY OF THE INVENTION

In one aspect, the invention provides a method for selecting a transformed plant cell comprising the steps of: a) contacting a population of plant cells comprising a transgenic plant cell transformed with a polynucleotide encoding dicamba monooxygenase with medium comprising auxin-like herbicide in an amount that inhibits the growth of cells from the population lacking the polynucleotide, wherein the polynucleotide comprises a nucleic acid sequence selected from: (1) a nucleic acid sequence encoding the polypeptide of SEQ ID NO:8, (2) a nucleic acid sequence comprising the sequence of SEQ ID NO:7, (3) a nucleic acid sequence that hybridizes to a complement of the nucleic acid sequence of SEQ ID NO:7 under conditions of 5×SSC, 50% formamide and 42° C., (4) a nucleic acid sequence having at least 70% sequence identity to the nucleic acid sequence of SEQ ID NO:7, and (5) a nucleic acid sequence encoding a polypeptide having at least 70% sequence identity to the polypeptide sequence of SEQ ID NO:8; and b) selecting the transformed plant cell from the population of plant cells based on tolerance exhibited by the transformed cell to the auxin-like herbicide. The population of cells may be contacted with medium comprising auxin-like herbicide any amount of time that allows selection of the transgenic cell. In certain embodiments, this may comprise at least 1-3 hours or may carried out indefinitely, for example, for tens or even hundreds of days. In one embodiment, the method may comprise culturing the population of plant cells on a medium lacking the auxin-like herbicide prior to step a) and/or between step a) and step b). The medium lacking the auxin-like herbicide may contain a cytokinin such as 6-benzyl amino purine (BAP). In particular embodiments, 6-benzyl amino purine may be in a concentration of about 10 mg/l of medium or less, including about 8, 6, 5, 4.5, 4, 3.5, 3, 2.5, 2, 1.5, 1, and about 0.5 mg/l or less.

In certain embodiments of the invention, a polynucleotide encoding dicamba monooxygenase is not genetically linked to a selectable or screenable marker gene other than dicamba monooxygenase. The polynucleotide encoding dicamba monooxygenase may be operatively linked to a chloroplast transit peptide. A method of the invention may also further comprise the step of: regenerating a transgenic plant from the transformed plant cell. In certain aspects of the invention, the transformed plant cell is from a dicot or monocot plant. Examples of dicot plants include alfalfa, beans, broccoli, cabbage, carrot, cauliflower, cotton, pea, rapeseed, and soybean and monocots include corn, onion, rice, sorghum, and wheat. In specific embodiments, the plant is a cotton, soybean or canola plant.

In certain aspects, an auxin-like herbicide is selected from the group consisting of a phenoxy carboxylic acid compound, a benzoic acid compound, a pyridine carboxylic acid compound, a quinoline carboxylic acid compound, and a benazolinethyl compound. In one embodiment, a phenoxy carboxylic acid compound is selected from the group consisting of 2,4-dichlorophenoxyacetic acid, 4-(2,4-dichlorophenoxy) butyric acid, and (4-chloro-2-methylphenoxy)acetic acid. In specific embodiments, a 2,4-dichlorophenoxyacetic compound, 4-(2,4-dichlorophenoxy) butyric acid, and/or (4-chloro-2-methylphenoxy)acetic acid is contained in the medium at a concentration of from about 0.001 mg/l to about 10 mg/l, including, for example, from about 0.01 mg/l to about 10 mg/l, from about 0.01 mg/l to about 5 mg/l, from about 0.1 mg/l to about 5 mg/l, from about 1 mg/l to about 5 mg/l, from about 1 mg/l to about 10 mg/l, from about 5 mg/l to about 10 mg/l, and from about 0.1 mg/l to about 3 mg/l. In other embodiments the benzoic acid is dicamba (3,6-dichloro-o-anisic acid) and is contained in the medium at a concentration of from about 0.001 mg/l to about 10 mg/l, including, for example, from about 0.01 mg/l to about 10 mg/l, from about 0.01 mg/l to about 3 mg/l, from about 0.001 mg/l to about 0.1 mg/l, from about 1 mg/l to about 10 mg/l, from about 2 mg/l to about 10 mg/l, and from about 0.001 mg/l to about 1 mg/l. In particular embodiments, the medium contains at least two auxin-like herbicides, for example, dicamba and 2,4-dichlorophenoxyacetic acid. In a method of the invention the population of cells may comprise a cotyledon explant and the transformed plant cell may be prepared by Agrobacterium-mediated transformation.

In another aspect, the invention provides a transgenic plant cell comprising a polynucleotide encoding dicamba monooxygenase and capable of growing in medium comprising 0.01 mg/l dicamba, wherein the dicamba monooxygenase is not genetically linked to a selectable or screenable marker gene and wherein the polynucleotide encoding dicamba monooxygenase comprises a nucleic acid sequence selected from the group consisting of (1) a nucleic acid sequence encoding the polypeptide of SEQ ID NO:8, (2) a nucleic acid sequence comprising the sequence of SEQ ID NO:7, (3) a nucleic acid sequence that hybridizes to a complement of the nucleic acid sequence of SEQ ID NO:7 under conditions of 5×SSC, 50% formamide and 42° C., (4) a nucleic acid sequence having at least 70% sequence identity to the nucleic acid sequence of SEQ ID NO:7, and (5) a nucleic acid sequence encoding a polypeptide having at least 70% sequence identity to the polypeptide sequence of SEQ ID NO:8. The cell may be defined in particular embodiments as prepared by a selection method disclosed herein The invention also provides a tissue culture comprising such a cell. The tissue culture may comprise the cell in a media comprising auxin-like herbicide in an amount that inhibits the growth of a plant cell of the same genotype as the transgenic plant cell that lacks the polynucleotide. The invention still further provides a transgenic plant regenerated from the transgenic plant cell.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
FIG. 1. Response of soybean explants to dicamba with or without addition of BAP. (A) On medium without dicamba (left) or with 0.1 mg/l dicamba (right), 13DAT. (B) Explants were inoculated and co-cultivated with Agrobacterium for 3 days, and then cultured on medium with 0 (top left), 0.1 (top center), 0.5 (top right), 1.0 (bottom left), 5.0 (bottom center) and 10 (bottom right) mg/l dicamba, 11DAT (14DAI). (C) Explants were also inoculated and co-cultivated with Agrobacterium for 3 d, and then cultured on medium with different levels of dicamba combined with BAP. From left to right: 0, 0.1, 1.0, and 5.0 mg/l dicamba. From top to bottom: 0, 1.0, 3.0, 5.0 mg/l BAP.

The invention provides in one aspect methods for the selection of transformed cells with auxin-like herbicides such as dicamba. The invention overcomes deficiencies in the prior art that previously required coupling of a gene conferring tolerance to auxin-like herbicides to a separate selectable marker gene in order to recover transformants. Direct selection eliminates the need for extraneous selectable marker genes, which can complicate transformation procedures and subsequent regulatory approval of transgenic plants. Efficient selection of transgenic cells is crucial because typically only a small number of cells are transformed in a transformation protocol. Cells that survive exposure to the selective agent may then be cultured in media that supports regeneration of plants to produce transgenic plants. By use of a nucleic acid encoding dicamba monooxygenase (DMO) in particular, the invention allows the selection and creation of transgenic plants exhibiting tolerance to auxin-like herbicides, which can be applied to fields containing herbicide tolerant plants for effective weed control.

Selection of transformed cells in accordance with the invention may be carried out, for example, by first introducing a DMO-encoding polynucleotide molecule into a selected target plant tissue; contacting cells containing the transformed plant cell with a medium containing an auxin-like herbicide in an amount that inhibits the growth of plant cells of the same genotype as the transformed plant cell not containing the DMO-encoding polynucleotide; and selecting a plant cell capable of growing in the medium. In this manner, a transgenic cell can be selected from a large population of non-transgenic cells. In an exemplary embodiment, selective media may be modified by including further substances such as growth regulators. Tissue may be maintained on a basic media with growth regulators until sufficient tissue is available to begin plant regeneration efforts, or following repeated rounds of manual selection, until the morphology of the tissue is suitable for regeneration, typically at least 2 weeks, then transferred to media conducive to maturation into plants. Cultures may be transferred every 2 weeks on this medium. Shoot development will signal the time to transfer to medium lacking growth regulators.

Numerous plant tissues are amenable to transformation. The plant cell may in certain embodiments come from a plant explant, which refers to a part excised from a plant that is capable of being transformed and subsequently regenerated into a transgenic plant. Typical explants include cell suspensions, meristems, mature or immature embryos, dry embryos, wet embryos, dried embryos, seeds, callus, cotyledons, cotyledonary nodes, leaves, or stems.

Once a transgenic cell has been selected and tissues grown therefrom, the presence of the exogenous DNA or "transgene(s)" in the regenerating tissue or plants can be confirmed using a variety of assays. Such assays include, for example, "molecular biological" assays, such as Southern and northern blotting and PCR™; "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

A. Nucleic Acids and Recombinant Constructs

1. Dicamba Monooxygenase (DMO)

In one embodiment of the present invention, a DNA construct expressing a dicamba monooxygenase (DMO) polypeptide is used as a selectable marker gene in plant cells. Exemplary DMO polypeptides are provided herein as SEQ ID Nos: 2, 4, 6, 8, 10 or 12. Exemplary nucleic acids encoding these sequences are provided as SEQ ID Nos: 1, 3, 5, 7, 9, or 11. Thus, in one embodiment of the invention, these sequences are used for the selection of transformed cells. As is well known in the art, homologous sequences and derivatives of these sequences may readily be prepared and used. For example, a nucleic acid may be used that encodes a DMO polypeptide having at least 70% sequence identity to a polypeptides provided as SEQ ID No: 2, 4, 6, 8, 10 or 12, including at least about 75%, 80%, 85%, 90%, 95%, 97%, 98%, 99% or greater identity to such sequences. A nucleic acid may be also be used that exhibits at least 70% sequence identity to a nucleic acid sequence provided as SEQ ID No: 1, 3, 5, 7, 9, or 11, including at least about 75%, 80%, 85%, 90%, 95%, 97%, 98%, 99% or greater identity to such sequences. In one embodiment, the identity is determined using the Sequence Analysis software package of the GCG Wisconsin Package (Accelrys, San Diego, Calif.), MEGAlign (DNAStar, Inc., 1228 S. Park St., Madison, Wis. 53715) with default parameters. Such software matches similar sequences by assigning degrees of similarity or identity.

A polynucleotide molecule that expresses a DMO polypeptide can be obtained by techniques well known in the art. Variants of DMOs having a capability to degrade auxin-like herbicides can readily be prepared and assayed for activity according to standard methods. Such sequences can also be identified by techniques know in the art, for example, from suitable organisms including bacteria that degrade auxin-like herbicides such as dicamba (U.S. Pat. No. 5,445,962; Krueger et al., 1989; Cork and Krueger, 1991; Cork and Khalil, 1995). One means of isolating a DMO sequence is by nucleic acid hybridization, for example, to a library constructed from the source organism, or by RT-PCR using mRNA from the source organism and primers based on the disclosed DMO. The invention therefore encompasses use of nucleic acids hybridizing under stringent conditions to a DMO encoding sequence described herein. One of skill in the art understands that conditions may be rendered less stringent by increasing salt concentration and decreasing temperature. Thus, hybridization conditions can be readily manipulated, and thus will generally be a method of choice depending on the desired results. An example of high stringency conditions is 5×SSC, 50% formamide and 42° C. By conducting a wash under such conditions, for example, for 10 minutes, those sequences not hybridizing to a particular target sequence under these conditions can be removed. One embodiment of the invention thus comprises use of a DMO-encoding nucleic acid that is defined as hybridizing under wash conditions of 5×SSC, 50% formamide and 42° C. for 10 minutes to a nucleic acid selected from SEQ ID NOS: 1, 3, 5, 7, 9, or 11.

SEQ ID NO: 1 shows DMO from *Pseudomonas maltophilia* optimized for expression in dicots using *Arabidopsis thaliana* codon usage. The polypeptide, predicted to have an Ala, Thr, Cys at positions 2, 3, 112, respectively, is given in SEQ ID NO:2. SEQ ID NO:3 shows another *Pseudomonas maltophilia* DMO optimized for expression in dicots and encoding the polypeptide of SEQ ID NO:4, predicted to have an Leu, Thr, Cys at positions 2, 3, 112, respectively. SEQ ID NO:5 shows the coding sequence and SEQ ID NO:6 the polypeptide for dicot optimized DMO predicted to have a Leu, Thr, Trp at positions 2, 3, 112, respectively. SEQ ID NOS:7 and 8 show the coding and polypeptide sequences for DMO predicted to have an Ala, Thr, Cys at position 2, 3, 112, respectively. SEQ ID NOS:9 and 10 show the dicot-optimized coding sequence and polypeptide sequences for DMO predicted to have an Ala, Thr, Trp at positions 2, 3, 112, respectively. SEQ ID NOS: 11 and 12 show coding sequence and polypeptide sequences for DMO from *Pseudomonas maltophilia* (US Patent Application No: 20030135879).

Variants can also be chemically synthesized using the known DMO polynucleotide sequences according to techniques well known in the art. For instance, DNA sequences may be synthesized by phosphoamidite chemistry in an automated DNA synthesizer. Chemical synthesis has a number of advantages. In particular, chemical synthesis is desirable because codons preferred by the host in which the DNA sequence will be expressed may be used to optimize expression. Not all of the codons need to be altered to obtain improved expression, but preferably at least the codons rarely used in the host are changed to host-preferred codons. High levels of expression can be obtained by changing greater than about 50%, most preferably at least about 80%, of the codons to host-preferred codons. The codon preferences of many host cells are known (PCT WO 97/31115; PCT WO 97/11086; EP 646643; EP 553494; and U.S. Pat. Nos. 5,689,052; 5,567,862; 5,567,600; 5,552,299 and 5,017,692). The codon preferences of other host cells can be deduced by methods known in the art. Also, using chemical synthesis, the sequence of the DNA molecule or its encoded protein can be readily changed to, for example, optimize expression (for example, eliminate mRNA secondary structures that interfere with transcription or translation), add unique restriction sites at convenient points, and delete protease cleavage sites.

Modification and changes may be made to the polypeptide sequence of a protein such as the DMO sequences provided herein while retaining enzymatic activity. The following is a discussion based upon changing the amino acids of a protein to create an equivalent, or even an improved, modified polypeptide and corresponding coding sequences. In particular embodiments of the invention, DMO sequences may be altered in this manner and used in the methods of the invention. The amino acid changes may be achieved by changing the codons of the DNA sequence.

It is known, for example, that certain amino acids may be substituted for other amino acids in a protein structure without appreciable loss of interactive binding capacity with structures such as binding sites on substrate molecules. Since it is the interactive capacity and nature of a protein that defines that protein's biological functional activity, certain amino acid sequence substitutions can be made in a protein sequence, and, of course, the underlying DNA coding sequence, and nevertheless obtain a protein with like properties. It is thus contemplated that various changes may be made in the DMO peptide sequences described herein and corresponding DNA coding sequences without appreciable loss of their biological utility or activity.

In making such changes, the hydropathic index of amino acids may be considered. The importance of the hydropathic amino acid index in conferring interactive biologic function on a protein is generally understood in the art (Kyte et al., 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte et al., 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent protein. In such changes, the substitution of amino acids whose hydrophilicity values are within ±2 is preferred, those which are within ±1 are particularly preferred, and those within ±0.5 are even more particularly preferred. Exemplary substitutions which take these and various of the foregoing characteristics into consideration are well known to those of skill in the art and include: arginine and lysine; glutamate and aspartate; serine and threonine; glutamine and asparagine; and valine, leucine and isoleucine.

2. Transformation Constructs

A DMO-encoding polynucleotide used in accordance with the invention as a selectable marker will typically be introduced into a cell as a construct comprising expression control elements necessary for the efficient expression of DMO. Methods of operatively linking expression control elements to coding sequences are well known in the art (Maniatis et al., 1982; Sambrook et al., 1989). Expression control sequences are DNA sequences involved in any way in the control of transcription. Suitable expression control sequences and methods of using them are well known in the art. A promoter in particular may be used, with or without enhancer elements, 5' untranslated region, transit or signal peptides for targeting of a protein or RNA product to a plant organelle, particularly to a chloroplast and 3' untranslated regions such as polyadenylation sites. One skilled in the art will know that various enhancers, promoters, introns, transit peptides, targeting signal sequences, and 5' and 3' untranslated regions (UTRs) are useful in the design of effective plant expression vectors, such as those disclosed, for example, in U.S. Patent Application Publication 2003/01403641.

Promoters suitable for the current and other uses are well known in the art. Examples describing such promoters include U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that may find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., 1987), the CaMV 35S promoter (Odell et al., 1985), the figwort mosaic virus 35S-promoter (Walker et al., 1987), the sucrose synthase promoter (Yang et al., 1990), the R gene complex promoter (Chandler et al., 1989), and the chlorophyll a/b binding protein gene promoter, etc. Particularly beneficial promoters for use with the present invention are CaMV35S, FMV35S, PClSV, AtAnt1 and P-AGRtu.nos promoters (also see Table 1).

Benefit may be obtained for the expression of heterologous genes by use of a sequence coding for a transit peptide. Transit peptides generally refer to peptide molecules that when linked to a protein of interest directs the protein to a particular tissue, cell, subcellular location, or cell organelle. Examples include, but are not limited to, chloroplast transit peptides, nuclear targeting signals, and vacuolar signals. A chloroplast transit peptide is of particular utility in the present invention for directing expression of a DMO enzyme to the chloroplasts. It is anticipated that DMO function will be facilitated by endogenous reductases and ferredoxins found in plant cells to degrade dicamba. Plant chloroplasts are particularly rich in reductases and ferredoxins. Accordingly, in a preferred embodiment for the production of transgenic dicamba-tolerant plants a sequence coding for a peptide may be used that will direct dicamba-degrading oxygenase into chloroplasts. Alternatively or in addition, heterologous reductase and/or ferredoxin can also be expressed in a cell.

DNA coding for a chloroplast targeting sequence may preferably be placed upstream (5') of a sequence coding for DMO, but may also be placed downstream (3') of the coding sequence, or both upstream and downstream of the coding sequence. A chloroplast transit peptide (CTP) in particular can be engineered to be fused to the N-terminus of proteins that are to be targeted into the plant chloroplast. Many chloroplast-localized proteins are expressed from nuclear genes as precursors and are targeted to the chloroplast by a CTP that is removed during the import steps. Useful CTPs can be identified from the primary amino acid sequence of such polypeptides. Examples of chloroplast proteins include the small subunit (RbcS2) of ribulose-1,5,-bisphosphate carboxylase, ferredoxin, ferredoxin oxidoreductase, the light-harvesting complex protein I and protein II, and thioredoxin F. It has been demonstrated in vivo and in vitro that non-chloroplast proteins may be targeted to the chloroplast by use of protein fusions with a CTP and that a CTP is sufficient to target a protein to the chloroplast. For example, incorporation of a suitable chloroplast transit peptide, such as, the *Arabidopsis thaliana* EPSPS CTP (Klee et al., 1987), and the *Petunia hybrida* EPSPS CTP (della-Cioppa et al., 1986) has been shown to target heterologous EPSPS protein sequences to chloroplasts in transgenic plants. Other exemplary chloroplast targeting sequences include the maize cab-m7 signal sequence (Becker et al., 1992; PCT WO 97/41228) and the pea glutathione reductase signal sequence (Creissen et al., 1991; PCT WO 97/41228). In the present invention, AtRbcS4 (CTP1), AtShkG (CTP2), AtShkGZm (CTP2synthetic), and PsRbcS, as well as others, disclosed in U.S. Provisional Appln. Ser. No. 60/891,675, in particular may be of benefit, for instance with regard to expression of a DMO polypeptide (e.g. SEQ ID NOs:17-28 for peptide sequences of CTPs and nucleic acid sequences that encode them).

A 5' UTR that functions as a translation leader sequence is a DNA genetic element located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and petunia heat shock protein leaders (U.S. Pat. No. 5,362,865), plant virus coat protein leaders, plant rubisco leaders, among others (Turner and Foster, 1995). In the present invention, 5' UTRs that may in particular find benefit are GmHsp, PhDnaK, AtAnt1, TEV, and L-Atnos (also see Table 1).

The 3' non-translated sequence, 3' transcription termination region, or poly adenylation region means a DNA molecule linked to and located downstream of a structural polynucleotide molecule and includes polynucleotides that provide polyadenylation signal and other regulatory signals capable of affecting transcription, mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA genes. An example of a 3' transcription termination region is the nopaline synthase 3' region (nos 3'; Fraley et al., 1983). The use of different 3' nontranslated regions is exemplified (Ingelbrecht et al., 1989). Polyadenylation molecules from a *Pisum sativum* RbcS2 gene (Ps.RbcS2-E9; Coruzzi et al., 1984) and T-AGRtu.nos (Rojiyaa et al., 1987, Genbank Accession E01312) in particular may be of benefit for use with the invention.

A DMO-encoding polynucleotide molecule expression unit can be linked to a second polynucleotide molecule in an expression unit containing genetic elements for a screenable/scorable marker or for a gene conferring a desired trait. Commonly used genes for screening presumptively transformed cells include β-glucuronidase (GUS), β-galactosidase, luciferase, and chloramphenicol acetyltransferase (Jefferson, 1987; Teeri et al., 1989; Koncz et al., 1987; De Block et al., 1984), green fluorescent protein (GFP) (Chalfie et al., 1994; Haseloff et al., 1995; and PCT application WO 97/41228). An AvGFP interrupted by StLS1 was used in the working examples for obtaining expression only in plant cells (also see Table 1).

The second polynucleotide molecule includes, but is not limited to, a gene that provides a desirable characteristic associated with plant morphology, physiology, growth and development, yield, nutritional enhancement, disease or pest resistance, or environmental or chemical tolerance and may include genetic elements comprising herbicide resistance (U.S. Pat. Nos. 6,803,501; 6,448,476; 6,248,876; 6,225,114; 6,107,549; 5,866,775; 5,804,425; 5,633,435; 5,463,175), increased yield (U.S. Pat. RE38,446; U.S. Pat. No. 6,716,474; U.S. Pat. No. 6,663,906; U.S. Pat. No. 6,476,295; U.S. Pat. No. 6,441,277; U.S. Pat. No. 6,423,828; U.S. Pat. No. 6,399,330; U.S. Pat. No. 6,372,211; U.S. Pat. No. 6,235,971; U.S. Pat. No. 6,222,098; U.S. Pat. No. 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658; 5,880,275; 5,763,245; 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; 6,506,962), virus resistance (U.S. Pat. Nos. 6,617,496; 6,608,241; 6,015,940; 6,013,864; 5,850,023; 5,304,730), nematode resistance (U.S. Pat. No. 6,228,992), bacterial disease resistance (U.S. Pat. No. 5,516,671), plant growth and development (U.S. Pat. Nos. 6,723,897; 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; 6,380,462), high oil production (U.S. Pat. Nos. 6,495,739; 5,608,149; 6,483,008; 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; 6,171,640), biopolymers (U.S. Pat. RE37,543; U.S. Pat. No. 6,228,623; U.S. Pat. No. 5,958,745 and U.S. Patent Publication No. US20030028917), environmental stress resistance (U.S. Pat. No. 6,072,103), pharmaceutical peptides and secretable peptides (U.S. Pat. Nos. 6,812,379; 6,774,283; 6,140,075; 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; 5,869,720) and biofuel production (U.S. Pat. No. 5,998,700). Any of these or other genetic elements, methods, and transgenes may be used with the invention as will be appreciated by those of skill in the art in view of the instant disclosure.

Alternatively, the second polynucleotide molecule can affect the above mentioned plant characteristic or phenotype by encoding a RNA molecule that causes the targeted inhibition of expression of an endogenous gene, for example, via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any polynucleotide molecule that encodes a transcribed RNA molecule that affects a phenotype or morphology change of interest may be useful for the practice of the present invention.

Expression units may be provided on T-DNAs between right border (RB) and left border (LB) regions of a first plasmid together with a second plasmid carrying T-DNA transfer and integration functions in *Agrobacterium*. The constructs may also contain plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404. However, other strains known to those skilled in the art of plant transformation can function in the present invention.

3. Preparation of Transgenic Cells

Transforming plant cells can be achieved by any of the techniques known in the art for introduction of transgenes into cells (see, for example, Miki et al., 1993). Examples of such methods are believed to include virtually any method by which DNA can be introduced into a cell. Methods that have been described include electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,635,055; 5,824,877; 5,591,616; 5,981,840; and 6,384,301; and protoplast transformation as illustrated in U.S. Pat. No. 5,508,184. Through the application of techniques such as these, the cells of virtually any plant species may be stably transformed and selected according to the invention and these cells developed into transgenic plants.

The most widely utilized method for introducing an expression vector into plants is based on the natural transformation system of *Agrobacterium* (for example, Horsch et al., 1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant (for example, Kado, 1991). Descriptions of *Agrobacterium* vector systems and methods for *Agrobacterium*-mediated gene transfer are provided by numerous references, including Gruber et al., supra, Miki et al., supra, Moloney et al., 1989, and U.S. Pat. Nos. 4,940,838 and 5,464,763. Other bacteria such as *Sinorhizobium, Rhizobium*, and *Mesorhizobium* that interact with plants naturally can be modified to mediate gene transfer to a number of diverse plants. These plant-associated symbiotic bacteria can be made competent for gene transfer by acquisition of both a disarmed Ti plasmid and a suitable binary vector (e.g. Broothaerts et al, 2005; U.S. patent application Ser. No. 11/749,583).

B. Tissue Cultures and Media

In accordance with the invention transgenic cells may be selected by using media containing an amount of an auxin-like herbicide that inhibits the growth of a cell lacking expression of a DMO polypeptide. "Media" refers to the numerous nutrient mixtures that are used to grow cells in vitro, that is, outside of the intact living organism. The medium is usually a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth will also vary among cultures initiated with the array of media that permit growth of that cell type.

Regenerating a transformed plant cell can be achieved by first culturing the explant on a shooting medium and subsequently on a rooting medium. In accordance with the invention these media generally include an auxin-like herbicide such as dicamba as the selection agent besides nutrients and growth regulators. A variety of media and transfer requirements can be implemented and optimized for each plant system for plant transformation and recovery of transgenic plants. Consequently, such media and culture conditions disclosed in the present invention can be modified or substituted with nutritionally equivalent components, or similar processes for selection and recovery of transgenic events, and still fall within the scope of the present invention.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture. Some cell types will grow and divide either in liquid suspension or on solid media.

Recipient cell targets include, but are not limited to, meristem cells, callus, immature embryos and gametic cells such as microspores pollen, sperm and egg cells. Any cell from which a transgenic plant, including a fertile transgenic plant, may be regenerated may be used in certain embodiments. For example, immature embryos may be transformed followed by selection and initiation of callus and subsequent regeneration of transgenic plants. Direct transformation of immature embryos obviates the need for long term development of recipient cell cultures. Meristematic cells (i.e., plant cells capable of continual cell division and characterized by an undifferentiated cytological appearance, normally found at growing points or tissues in plants such as root tips, stem apices, lateral buds, etc.) may also be used as a recipient plant cell. Because of their undifferentiated growth and capacity for organ differentiation and totipotency, a single transformed meristematic cell could be recovered as a whole transformed plant.

Somatic cells are of various types. Embryogenic cells are one example of somatic cells which may be induced to regenerate a plant through embryo formation. Non-embryogenic cells are those which typically will not respond in such a fashion.

Certain techniques may be used that enrich recipient cells within a cell population. For example, Type II callus development, followed by manual selection and culture of friable, embryogenic tissue, generally results in an enrichment of recipient cells for use in, for example, micro-projectile transformation.

Selection in culture may be carried out following plant cell transformation using a variety of transformation methods. *Agrobacterium* transformation followed by selection is described in the working examples below. In addition, exemplary procedures for selection of transformed cells prepared by microprojectile bombardment are provided as follows:

1. Tissue (suspension) is plated on filters, microprojectile bombarded and then filters transferred to culture medium. After 2-7 days, filters are transferred to selective medium. Approximately 3 weeks after bombardment, tissue is picked from filters as separate callus clumps onto fresh selective medium.

2. As in 1 above, except after bombardment the suspension is put back into liquid—subjected to liquid selection for 7-14 days and then pipetted at a low density onto fresh selection plates.

3. Callus is bombarded while sitting directly on medium or on filters. Cells are transferred to selective medium 1-14 days after particle bombardment. Tissue is transferred on filters 1-3 times at 2 weeks intervals to fresh selective medium. Callus is then briefly put into liquid to disperse the tissue onto selective plates at a low density.

4. Callus tissue is transferred onto selective plates one to seven days after DNA introduction. Tissue is subcultured as small units of callus on selective plates until transformants are identified.

In certain embodiments, recipient cells are selected following growth in culture. Cultured cells may be grown either on solid supports or in the form of liquid suspensions. In either instance, nutrients may be provided to the cells in the form of media, and environmental conditions controlled. There are many types of tissue culture media comprised of amino acids, salts, sugars, growth regulators and vitamins. Most of the media employed in the practice of the invention will have some similar components, while the media can differ in composition and proportions of ingredients according to known tissue culture practices. For example, various cell types usually grow in more than one type of media, but will exhibit different growth rates and different morphologies, depending on the growth media. In some media, cells survive but do not divide. Media composition is also frequently optimized based on the species or cell type selected.

Various types of media suitable for culture of plant cells have been previously described. Examples of such media are defined below. In some embodiments, it may be preferable to use a media with a somewhat lower ammonia/nitrate ratio such as N6 to promote generation of recipient cells by maintaining cells in a proembryonic state capable of sustained divisions. In certain embodiments of the present invention, Woody Plant Medium (WPM) was used (Lloyd and McCown, 1981).

The method of maintenance of cell cultures may contribute to their utility as sources of recipient cells for transformation. Manual selection of cells for transfer to fresh culture medium, frequency of transfer to fresh culture medium, composition of culture medium, and environment factors including, but not limited to, light quality and quantity and temperature are all factors in maintaining callus and/or suspension cultures that are useful as sources of recipient cells. Alternating callus between different culture conditions may be beneficial in enriching for recipient cells within a culture. For example, cells may be cultured in suspension culture, but transferred to solid medium at regular intervals. After a period of growth on solid medium, cells can be manually selected for return to liquid culture medium. Repeating this sequence of transfers to fresh culture medium may be used to enrich for recipient cells. Passing cell cultures through a 1.9 mm sieve may also be useful to maintain the friability of a callus or suspension culture and enriching for transformable cells when such cell types are used.

C. Transgenic Plants

Once a transgenic cell has been selected, the cell can be regenerated into a transgenic plant using techniques well known in the art. The transformed plants can be subsequently analyzed to determine the presence or absence of a particular nucleic acid of interest contained on a DNA construct. Molecular analyses can include, but are not limited to, Southern blots (Southern, 1975), northern blot analysis, western blot analysis, or PCR analyses, immunodiagnostic approaches, and field evaluations. These and other well known methods can be performed to confirm the stability of the transformed plants produced by the methods disclosed. These methods are well known to those of skill in the art (Sambrook et al., 1989).

Transgenic plants tolerant to auxin-like herbicides can be produced. In particular, economically important plants, including crops, fruit trees, and ornamental plants and trees that are currently known to be injured by auxin-like herbicides can be transformed with DNA constructs of the present invention so that they become tolerant to the herbicide. Plants that are currently considered tolerant to auxin-like herbicides can be transformed to increase their tolerance to the herbicide. Examples of plants that may in particular find use with the current invention include, but are not limited to, alfalfa, beans, broccoli, cabbage, carrot, cauliflower, celery, cotton, cucumber, eggplant, lettuce, melon, pea, pepper, pumpkin, radish, rapeseed, spinach, soybean, squash, tomato, watermelon, corn, onion, rice, sorghum, wheat, rye, millet, sugarcane, oat, triticale, switchgrass, and turfgrass.

Once a transgenic plant containing a transgene has been prepared, that transgene can be introduced into any plant sexually compatible with the first plant by crossing, without the need for ever directly transforming the second plant. Therefore, as used herein the term "progeny" denotes the offspring of any generation of a parent plant prepared in accordance with the instant invention, wherein the progeny comprises a selected DNA construct prepared in accordance with the invention. A "transgenic plant" may thus be of any generation. "Crossing" a plant to provide a plant line having one or more added transgenes or alleles relative to a starting plant line, as disclosed herein, is defined as the techniques that result in a particular sequence being introduced into a plant line by crossing a starting line with a donor plant line that comprises a transgene or allele of the invention. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

D. Definitions

As used herein, the term "transformed" refers to a cell, tissue, organ, or organism into which has been introduced a foreign polynucleotide molecule, such as a construct. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule.

"Contacting" the transformed plant cell with a tissue culture medium containing an auxin-like herbicide can be achieved by culturing the plant cell in a plant tissue culture medium containing an auxin-like herbicide.

"Tissue culture medium" refers to liquid, semi-solid, or solid medium used to support plant growth and development in a non-soil environment. Suitable plant tissue culture media are known to one of skill in the art may include MS-based media (Murashige and Skoog, 1962) or N6-based media (Chu et al., 1975) supplemented with additional plant growth regulators such as auxins, cytokinins, kinetin, ABA, and gibberellins. Other media additives can include but are not limited to amino acids, macroelements, iron, microelements, inositol, vitamins and organics, carbohydrates, undefined media components such as casein hydrolysates, with or without an appropriate gelling agent such as a form of agar, such as a low melting point agarose or Gelrite® if desired for preparing semi-solid or solid medium. Those of skill in the art are familiar with the variety of tissue culture media, which when supplemented appropriately, support plant tissue growth and development and are suitable for plant transformation and regeneration. These tissue culture media can either be purchased as a commercial preparation or custom prepared and modified. Examples of such media would include but are not limited to Murashige and Skoog (1962), N6 (Chu et al., 1975), Linsmaier and Skoog (1965), Uchimiya and Murashige (1962), Gamborg's media (Gamborg et al., 1968), D medium (Duncan et al., 1985), McCown's Woody plant media (McCown and Lloyd, 1981), Nitsch and Nitsch (1969), and Schenk and Hildebrandt (1972) or derivations of these media supplemented accordingly. Those of skill in the art are aware that media and media supplements such as nutrients and growth regulators for use in transformation and regeneration and other culture conditions such as light intensity during incubation, pH, and incubation temperatures can be optimized for a plant of interest.

"Auxin-like herbicides" are also called auxinic or growth regulator herbicides or Group 4 herbicides (based on their mode of action). These herbicides mimic or act like the natural plant growth regulators called auxins. Auxins include natural hormones such as indole acetic acid and naphthalene acetic acid, both of which are responsible for cell elongation in plants. The mode of action of the auxinic herbicides is that they appear to affect cell wall plasticity and nucleic acid metabolism, which can lead to uncontrolled cell division and growth. The group of auxin-like herbicides includes four chemical families: phenoxy, carboxylic acid (or pyridine), benzoic acid, and the newest family quinaline carboxylic acid. Phenoxy carboxylic acids: the phenoxy herbicides are most common and have been used as herbicides since the 1940s when (2,4-dichlorophenoxy)acetic acid (2,4-D) was discovered. Other examples include 4-(2,4-dichlorophenoxy) butyric acid (2,4-DB), 2-(2,4-dichlorophenoxy) propanoic acid (2,4-DP), (2,4,5-trichlorophenoxy)acetic acid (2,4,5-T), 2-(2,4,5-Trichlorophenoxy) Propionic Acid (2,4,5-TP), 2-(2, 4-dichloro-3-methylphenoxy)-N-phenylpropanamide (cloimeprop), (4-chloro-2-methylphenoxy)acetic acid (MCPA), 4-(4-chloro-o-tolyloxy) butyric acid (MCPB), and 2-(4-chloro-2-methylphenoxy) propanoic acid (MCPP).

Pyridine carboxylic acids: the next largest chemical family is the carboxylic acid herbicides, also called pyridine herbicides. Examples include 3,6-dichloro-2-pyridinecarboxylic acid (Clopyralid), 4-amino-3,5,6-trichloro-2-pyridinecarboxylic acid (picloram), (2,4,5-trichlorophenoxy)acetic acid (triclopyr), and 4-amino-3,5-dichloro-6-fluoro-2-pyridyloxyacetic acid (fluoroxypyr). Benzoic acids: Examples include 3,6-dichloro-o-anisic acid (dicamba) and 3-amino-2, 5-dichlorobenzoic acid (choramben). Quinaline carboxylic acids: the fourth and newest chemical family of the auxinic herbicides is the quinaline carboxylic acid family. Example includes 3,7-dichloro-8-quinolinecarboxylic acid (quinclorac). This herbicide is unique in that it also will control some grass weeds, unlike the other auxin-like herbicides which essentially control only broadleaf or dicotyledonous plants.

The other herbicide in this category is 7-chloro-3-methyl-8-quinolinecarboxylic acid (quinmerac).

"Auxin-like herbicide effect" means injury symptoms caused by auxin-like herbicides. These include epinastic bending and twisting of stems and petioles, leaf cupping and curling, and abnormal leaf shape and venation. All of these herbicides translocate, with some translocating more than others. Some of these herbicides have soil activity and some can persist in soil for fairly long time periods. Due to their effect, they are used widely on many crops including small grain cereals, corn, rice, and other grass crops, turf, rangeland, non-crop, and industrial sites.

"Selecting" the transformed plant cell that is tolerant to an auxin-like herbicide can be achieved by methods described in the present invention. Briefly, at least some of the plant cells in a population of starting cells are transformed with a DNA construct containing a DMO-encoding polynucleotide molecule. The resulting population of plant cells is placed in a culture medium containing an auxin-like herbicide at a concentration selected so that transformed plant cells will grow, whereas untransformed plant cells will not. Suitable concentrations of an auxin-like herbicide can be determined empirically. Before selecting, explants may be cultured on a medium without auxin-like herbicide. Such medium is called delay medium. Explants may be placed on delay medium to allow for some time to grow before being placed on the selection medium. Selection regimes could be optimized depending upon a particular auxin-like herbicide and the explant system. Often multiple steps of selection are used and varying amounts of selection agent can be used in each step.

"Tolerant" means that transformed plant cells are able to survive and regenerate into plants when placed in a culture medium containing a level of an auxin-like herbicide that prevents untransformed cells from doing so. "Tolerant" also means that transformed plants are able to grow after application of an amount of an auxin-like herbicide that inhibits the growth of untransformed plants.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Preparation of DMO-Encoding Polynucleotide Constructs

Several binary vectors were prepared for testing the ability of DMO-encoding polynucleotide molecules to allow selection of transformed soybean cells. Genetic elements used for preparing the binary vectors are given in Table 1 and include a CaMV 35S promoter and enhancer (U.S. Pat. Nos. 5,322,938; 5,352,605; 5,359,142; and 5,530,196); GmHsp untranslated leader from the Hsp17.9 gene of *Glycine max* (U.S. Pat. No. 5,659,122); AvGFPI coding region for the first 126.3 amino acids of the GFP protein from *Aequorea victoria* (U.S. Pat. Nos. 5,491,084; 6,146,826) with a serine to threonine change at amino acid 65 and optimized for plant expression; a StLS1 second intron from the LS1 gene of *Solanum tuberosum* (Eckes et al., 1986); an AvGFPII coding region for the last 112.6 amino acids of the GFP protein from *Aequorea victoria* (U.S. Pat. Nos. 5,491,084; 6,146,826) optimized for plant expression; a T-Atnos 3' untranslated region of the nopaline synthetase gene from *Agrobacterium tumefaciens* (Rojiyaa et al., 1987, GenBank Accession E01312); a FMV Figwort Mosaic Virus 35S promoter (U.S. Pat. Nos. 6,051,753; 5,378,619); a PhDnaK untranslated leader from Hsp70 gene of *Petunia hybrida* (U.S. Pat. No. 5,362,865); and an AtRbcS4 (CTP1) coding region for *Arabidopsis* SSU1A transit peptide. The latter element includes the transit peptide, 24 amino acids of the mature protein, and a repeat of the last 6 amino acids of the transit peptide (U.S. Pat. No. 5,728,925). Also used were an AtShkG (CTP2) coding region for *Arabidopsis thaliana* 5-enolpyruvylshikimate-3-phosphate synthase (EPSPS) transit peptide. This element varies from the wild-type sequence (Klee et al., 1987) in that the last codon was changed from GAG (glutamic acid) to TGC (cysteine). An AtShkGzmcodon (CTP2syn) element was used which is the same as AtShkG (CTP2) but optimized for plant expression using *Zea mays* codons (see SEQ ID NO:14 of WO04009761). A PmDMOCys112Atcodon region for dicamba monooxygenase from *Pseudomonas maltophilia* was used (US Patent Application 20030115626) having a cysteine at 112 position and optimized for dicot expression using *Arabidopsis thaliana* codons (SEQ ID NOs: 1, 3, 7). Also used for construct design were a PmDMOTrp112Atcodon coding region for dicamba monooxygenase from *Pseudomonas maltophilia* (US patent application 20030115626) having a tryptophan (Trp) at 112 position and optimized for dicot expression using *Arabidopsis thaliana* codons (SEQ ID NOs: 5, 9); a PsRbcS2: 3' polyadenylation region from the RbcS2-E9 gene of *Pisum sativum* (Coruzzi et al., 1984); an AtAnt1 promoter/intron and leader of adenine nucleotide translocator 1 gene from *Arabidopsis thaliana*; an AtaroA-CP4 coding region for non-naturally occurring aroA-CP4 (U.S. Pat. No. 5,633,435) engineered for expression in plants; a TEV 5' untranslated leader from the Tobacco Etch RNA virus (Carrington and Freed, 1990); a PsRbcS chloroplast transit peptide from ribulose 1,5-bisphosphate carboxylase small subunit of pea and first 24 amino acids of the mature rubisco protein (Coruzzi et al., 1984); a P-Atnos promoter for nopaline synthetase of *Agrobacterium tumefaciens* pTiT37 (GenBank Accession V00087; Depicker et al, 1982; Bevan et al., 1983); a L-At.nos 5' untranslated region from the nopaline synthetase gene of *Agrobacterium tumefaciens* pTiT37 (GenBank Accession V00087; Bevan et al., 1983), and a PClSV promoter for the full length transcript of peanut chlorotic streak virus. The latter element has a duplication of 179 nt in direct repeats with 6 nt between the repeat followed by the 70 bp region containing the TATA box (U.S. Pat. No. 5,850,019). Different CTPs and DMO-encoding polynucleotide molecule variants are summarized in Table 2.

TABLE 1

Genetic elements used for constructing T-DNAs

| Construct | Expression Unit 1 | | | | | | Expression Unit 2 | | | | |
|---|---|---|---|---|---|---|---|---|---|---|---|
| | Promoter | 5'UTR | CR | Intron | CR | PolyA | Promoter | 5' UL | TS | CR | Poly A |
| pMON73690 | CaMV | GmHsp | AvGFPI | StLS1 | AvGFPII | T-Atnos | FMV | PhDnaK | None | PmDMOCys$_{112}$Atcodon | PsRbcS2 |
| pMON73691 | CaMV | GmHsp | AvGFPI | StLS1 | AvGFPII | T-Atnos | FMV | PhDnaK | AtShkG | PmDMOCys$_{112}$Atcodon | PsRbcS2 |
| pMON73696 | CaMV | GmHsp | AvGFPI | StLS1 | AvGFPII | T-Atnos | FMV | PhDnaK | AtRbcS4 | PmDMOTrp$_{112}$Atcodon | PsRbcS2 |
| pMON73698 | CaMV | GmHsp | AvGFPI | StLS1 | AvGFPII | T-Atnos | FMV | PhDnaK | AtRbcS4 | PmDMOCys$_{112}$Atcodon | PsRbcS2 |

| Construct | Promoter | 5'UR | TS | CR | PolyA | Promoter | 5' UL | TS | CR | Poly A |
|---|---|---|---|---|---|---|---|---|---|---|
| pMON73724 | AtAnt1 | AtAnt1 | At.ShkG | At.aroA-CP4 | PsRbcS2 | PClSV | TEV | AtShkGZmcodon | PmDMOTrp$_{112}$ Atcodon | Atnos |

| Construct | First T-DNA | | | | | Second T-DNA | | | | |
|---|---|---|---|---|---|---|---|---|---|---|
| | Promoter | 5'UTR | TS | CR | PolyA | Promoter | 5' UL | TS | CR | Poly A |
| pMON58498 | PClSV | TEV | PsRbcS | PmDMOCys$_{112}$ | PsRbcS2 | FMV | PhDnaK | AtShkG | AtaroA-CP4 | PsRbcS2 |
| pMON84254 | PClSV | TEV | PsRbcS | PmDMOCys$_{112}$ | PsRbcS2 | P-Atnos | L-Atnos | None | Sh.bar | T-Atnos |

Key:
5'UTR: 5' untranslated region;
CR: coding region;
Poly A: polyadenylation region; and
TS: transit sequence.

TABLE 2

Chloroplast transit peptides and DMO-encoding polynucleotides used in binary vectors.

| Construct | CTP variant | DMO variant | SEQ ID | Length | Predicted aa at position 2 | Predicted aa at position 112 |
|---|---|---|---|---|---|---|
| pMON73690 | None | DMO-Cys$_{112}$ and codon optimized for dicots | 1 | 1023 | Ala | Cys |
| pMON73691 | CTP2 | DMO-Cys$_{112}$ and codon optimized for dicots | 3 | 1023 | Leu | Cys |
| pMON73696 | CTP1 | DMO-Trp$_{112}$ and codon optimized for dicots | 5 | 1023 | Leu | Trp |
| pMON73698 | CTP1 | DMO-Cys$_{112}$ and codon optimized for dicots | 3 | 1023 | Leu | Cys |
| pMON58498 | PsRbcS | DMO-Cys$_{112}$ | 7 | 1023 | Ala | Cys |
| pMON84254 | PsRbcS | DMO-Cys$_{112}$ | 7 | 1023 | Ala | Cys |
| pMON73724 | CTP2Zm | DMO-Trp$_{112}$ and codon optimized for dicots | 9 | 1023 | Ala | Trp |

In the case of pMON73690, pMON73691, pMON73696, and pMON73698, the DMO-encoding polynucleotide molecule was linked to the screenable marker GFP and provided on the same T-DNA to show that the DMO-encoding polynucleotide molecule can be used with another gene. In case of pMON58498, pMON84254, and pMON73724, the DMO-encoding polynucleotide molecule was unlinked from the other transgene (selectable marker or agronomic trait gene) by separating them on two T-DNAs.

Example 2

Development of Selection Method

Mature seeds of soybean [*Glycine max* (L.) Merrill] cv. A3525 were imbibed, sterilized, and germinated at room temperature as set forth below. Other examples of soybean genotypes that can readily be used include, but are not limited to, Jack, Williams, Bert, Thorne, Granite, Lambert, Chapman, and Kunitz. Briefly, dry seeds (about 770 g) were soaked for 3 min in 2 L of 200 ppm sodium hypochlorite solution made from commercially available Clorox. The solution was drained and the seeds were set side for about 2 h. About 2 L of bean sterilization/germination medium was then added to the seeds. After about 9-10 h, seeds were ready for hand excision of explants. The bean germination medium contained the following in mg/L—$NH_4NO_3$: 240, $KNO_3$: 505, $CaCl_2.2H_2O$: 176, $MgSO_4.7H_2O$: 493, $KH_2PO_4$: 27, $H_3BO_3$: 1.86, $Na_2MoO_4.2H_2O$: 0.216, $MnSO_4.H_2O$: 5.07, $ZnSO_4.7H_2O$: 2.58, $FeSO_4.7H_2O$: 2.502, KI: 0.249, $Na_2EDTA.2H_2O$: 3.348, $CuSO_4.5H_2O$: 0.0008, $CoCl_2.6H_2O$: 0.0008, B1: 1.34, B3: 0.5, B6: 0.82, Bravo (75% WP; Diamond Shamrock Company, Cleveland, Ohio): 30, Captan (50% WP; Micro Flo Company, Lakeland, Fla.): 30, Cefotaxime: 125, and Sucrose: 25000, pH 5.8).

For machine excision of the explants, seeds were treated with 2 L of 200 ppm sodium hypochlorite solution for 15 min. After draining the solution the seeds were rinsed with 2 L of sterile distilled water for 1 min. The machine and method for mechanical excision are described in the US Patent Appln. Pub. 20050005321. Briefly, imbibed seeds were run through three sets of rollers in the machine, with sterile distilled water running over them, and crushed. A mixture of cotyledons, seed coats and the explants (embryo axis) is collected and sieved by either hand or by using an auto-sieving device to recover the explants. The explants were rinsed with 0.05% ethanol for 1 min, followed by two rinses with sterile distilled water for removing more debris.

The binary vectors described above were mobilized into disarmed *Agrobacterium tumefaciens* strain C58 (ABI). *Agrobacterium* inoculum for infection was prepared as follows: 250 ml of LB medium (Luria-Bertani; Difco, Detroit, Mich.) containing 50 mg/l kanamycin (Sigma, St. Louis, Mo.) and 75 mg/l spectinomycin (Sigma, St. Louis, Mo.) was inoculated with 0.5 ml of *Agrobacterium* stock in glycerol (Acros Organics, Geel, Belgium) and was shaken at 200 rpm at 28° C. for approximately 20-22 h until the $OD_{660}$ reached 0.8 to 1.0. The *Agrobacterium* broth was then centrifuged for 25 min at 3500 rpm (about 3565 g) at 2-4° C. After removing the supernatant, the *Agrobacterium* pellet was re-suspended in inoculation medium containing ⅖× of the macro nutrients, ¹⁄₁₀× of the micro nutrients and vitamins of Gamborg's B5 medium, supplemented with 3.9 g/l MES (Sigma, St. Louis, Mo.), and 30 g/l glucose (PhytoTechnology Laboratories, Shawnee Mission, Kans.), pH 5.4. Lipoic acid (Sigma, St. Louis, Mo.) was added to the *Agrobacterium* suspension to a final concentration of 0.25 mM after the density of the *Agrobacterium* cell suspension was adjusted to an $OD_{660}$ of 0.30 to 0.35.

*Agrobacterium*-infection and co-cultivation of the explants were conducted as follows: about 100 excised explants were dispensed into the lid of a sterile plastic culture vessel PLANTCON (MP Biomedicals, LLC, Irvine, Calif.). Five ml of *Agrobacterium* inoculum was added to the explants in each PLANTCON lid. The explants were then sonicated for 20 sec in a sonicator (Ultrasonic Multi Cleaner, Model W-113, Honda, Japan). One piece of Whatmann #1 filter paper (Whatman Inc., Clifton, N.J.) cut to the size of the PLANTCON bottom was placed in the bottom part of the PLANTCON. The explants were transferred from the lid onto the filter paper with the *Agrobacterium* inoculum. The PLANTCON s were then incubated in a Percival incubator at 16 h light (at about 85-90 µE) and 8 h dark photoperiod and at 23° C. for 2 to 4 d for co-cultivation.

After a co-cultivation period of 2-4 days, explants were first cultured on a medium without dicamba (delay medium) for 3-5 d before being transferred to the selection medium with dicamba. Until transfer from delay medium to selection medium, the explants were kept in the same PLANTCON used for co-cultivation, but 10 or 12 ml of the delay medium was added to each PLANTCON. Alternatively, the explants were transferred to new PLANTCONs, each containing one piece of autoclaved felt (Jo-Ann Fabrics & Crafts, Madison, Wis.)) and 30 ml of the delay medium. The delay medium contained modified wood plants medium (Lloyd and McCown, 1981) supplemented with 1 or 5 mg/l BAP (6-benzyl Amino Purine), 200 mg/l carbenicillin (PhytoTechnology Laboratories, Shawnee Mission, Kans.), 200 mg/l cefotaxime (Hospira, Lake Forest, Ill.) and 100 mg/l ticarcillin (Duchefa, The Netherlands). BAP may help maintain the auxin-cytokinin ratio as dicamba is an auxin herbicide, and promote production of multiple shoots from the apical meristem. Other suitable cytokinins that can be useful in practicing the present invention include: Adenine cytokinins (e.g., kinetin, zeatin, benzyl adenine (i.e. 6-Benzyl aminopurine), adenine and Phenylurea cytokinins (e.g., N,N'-diphenylurea), and Thidiazuron (TDZ).

Selection was conducted in a liquid or on a semi-solid medium. The selection medium was the delay medium absent BAP and contained different concentrations of dicamba. For selection in liquid medium, 50 or 60 ml of the selection medium and one piece of foam sponge (Wisconsin Foam Products, Madison, Wis.) having 5 parallel slits were placed in each Plantcon. Twenty-five explants were implanted into the slits in an upward position such that apical meristem faced upward. Every two to three weeks, old medium was replaced with the fresh medium.

Semi-solid medium was prepared by adding 4 g/l AgarGel (Sigma, St. Louis, Mo.) to the liquid medium. For selection on semi-solid selection medium, the explants were individually implanted into the medium in PLANTCONs. At the late stage of the selection and shoot development (approximately 4 weeks on the selection medium), 20 ml of the liquid selection medium was optionally overlaid on the semi-solid medium. Elongated shoots with expanded trifoliate foliage leaves started to develop after the explants had been cultured on the selection medium for about 4 to 5 weeks. These tolerant shoots were detached from the original explants when they were about and over 2 cm long and transferred to the liquid or semi-solid root induction medium.

Figure 5:
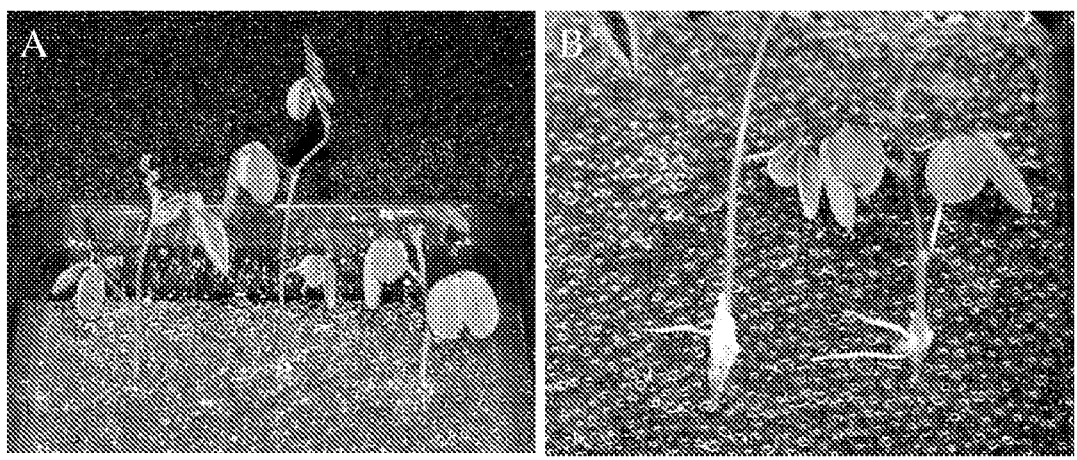
FIG. 5. Detached resistant shoots were cultured on the liquid rooting medium with small glass beads (A) as support material and almost all of the shoots could produce roots. (B) Semi-solid medium can also be used for root induction.

The medium for root induction was the same as for shoot development and was also supplemented with dicamba to reduce the frequency of escapes. Alternatively, Bean Rooting Medium (BRM) supplemented with 0.01 mg/l dicamba was used for root induction. This medium contained ½ strength of MS salts, MS vitamins, 100 mg/l inositol, 100 mg/l cysteine, 30 mg/l sucrose and 100 mg/l ticarcilin and was solidified with 8 g/l washed agar. For root induction in the liquid medium, enough small glass beads (Inotech Biosystems International Inc., Dottikon, Switzerland) and 60 ml of the rooting medium were placed in each PLANTCON such that the medium and beads were at the same level. Up to nine detached shoots were inserted into the beads for liquid root induction or in semi-solid medium in each PLANTCON. Almost all shoots could produce roots on the rooting medium in 1-2 weeks (FIG. 5). However, only those shoots in which the existing and newly developed leaves remained expanded and grew vigorously were transferred to soil for growing to maturity. All cultures were kept under fluorescent light with a photoperiod of 16 h with light intensity of about 20-70 µE at 27-28° C. until $R_0$ plants were transferred to the soil.

Figure 4:
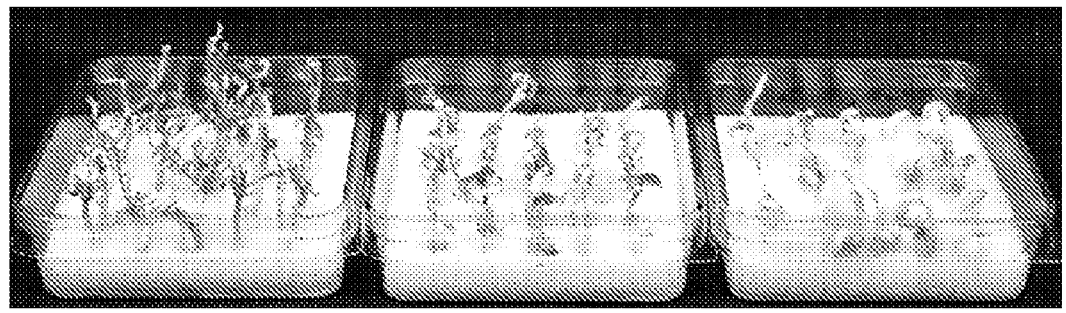
FIG. 4. Response of explants cultured on medium containing 0.01 (left), 0.02 (center) and 0.05 mg/l dicamba, 23DAT (29 DAI).

In one study, soybean cells transformed with pMON73691 were selected on 0.01 to 0.1 mg/l of dicamba in selection medium (FIGS. 1 A & B; FIG. 4). Shoots coming out of explants grown on selection medium with 0.05 or 0.1 mg/l dicamba did not have much growth and eventually bleached out and no tolerant shoots were obtained. However, in selection medium containing 0.01 mg/l dicamba, 30 dicamba-tolerant shoots were harvested from 800 explants. Twelve of these formed roots on rooting medium and were transferred to the soil. Ten of these were tested for DMO-encoding polynucleotides and seven were found to be positive. At a dicamba level of 0.02 mg/l, few tolerant shoots were harvested. These results suggested that a dicamba concentration of 0.01 mg/l or lower was most efficacious for selecting dicamba-tolerant shoots. This level could readily be altered by one skill in the art for particular studies, however, depending upon the nature of the explant, construct, and other variables.

Figure 2:
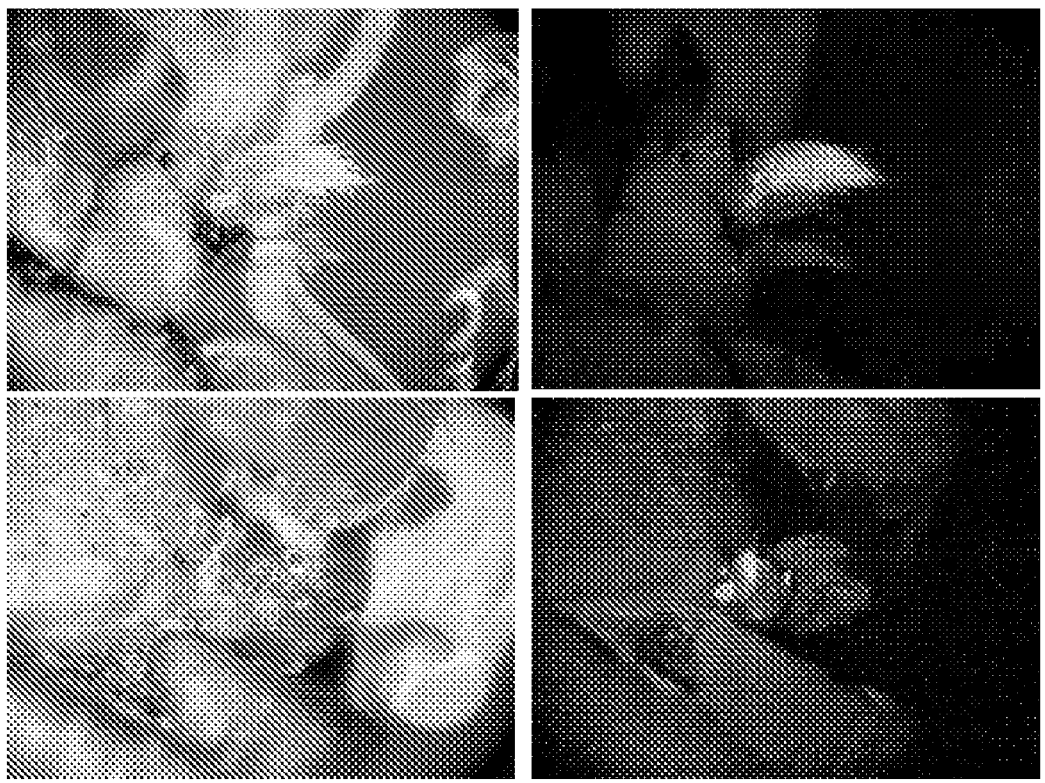
FIG. 2. Examples of explants with GFP+ small bud (top) or sectors (bottom) in experiment (Exp508) with dicamba selection. The pictures were taken at 45 DAI under regular bright field (left) or UV light for detecting GFP expression (right).
Figure 3:
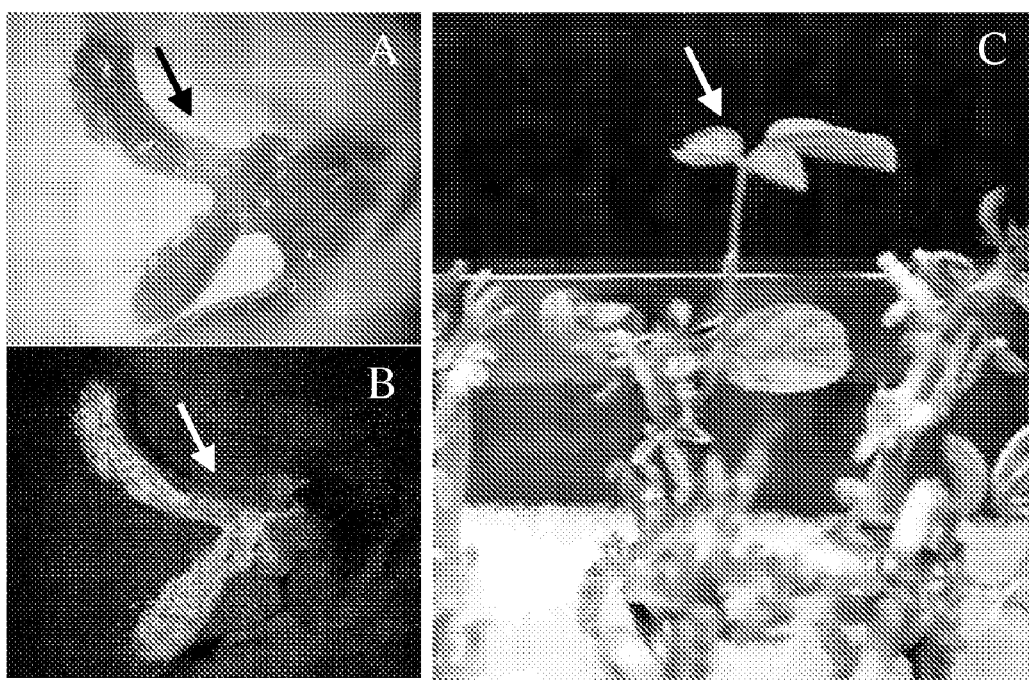
FIG. 3. GFP-positive event from dicamba selection. (A) A small shoot observed 29 DAI under regular dissecting microscope. (B) The same bud showed GFP-expression as observed under fluorescent light for detecting GFP. (C) The small shoot in A&B developed into a resistant elongated shoot (arrow), 48DAI.
Figure 6:
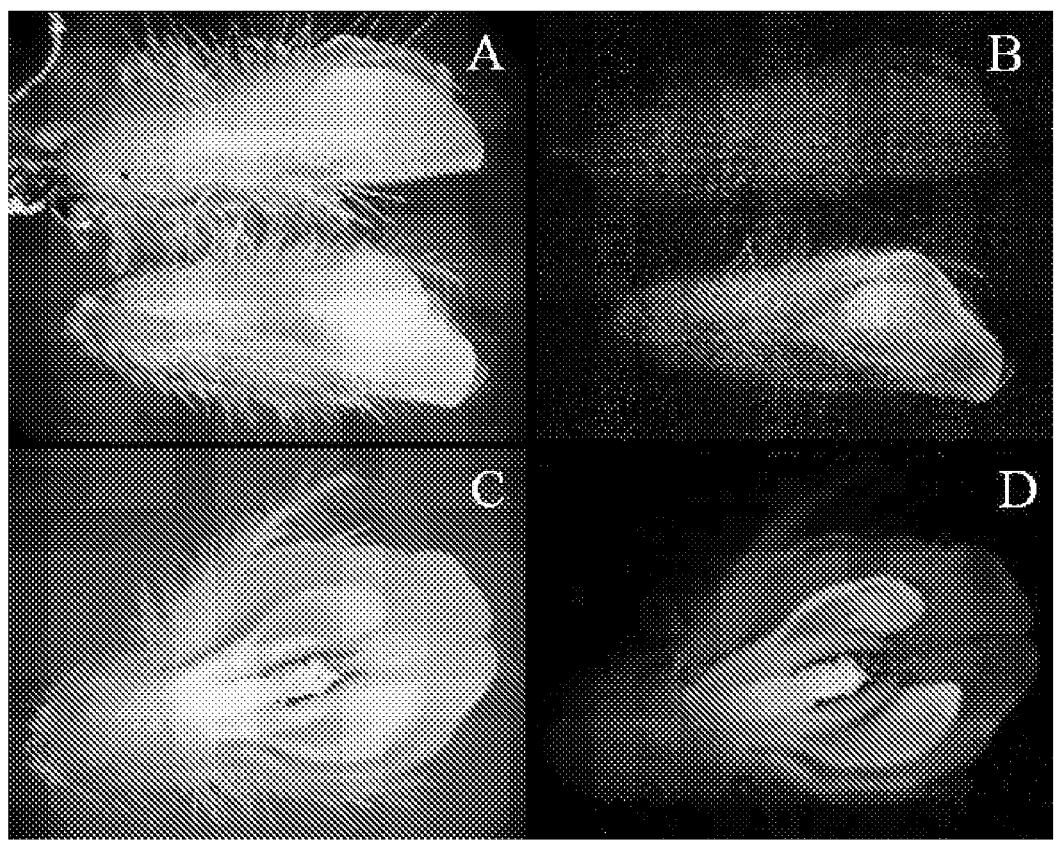
FIG. 6. (A) Young soybean flowers from a transgenic plant with CP4 and GUS gene (top) and a plant transformed with pMON73691 through dicamba selection and also carrying a GFP gene (bottom). (B) The same two flowers observed under a dissecting microscope equipped with fluorescent light to detect GFP expression. GFP expression was observed on the flower transformed with pMON73691, which contains DMO and GFP genes. (C, D) The same flower transformed with pMON73691 was opened to show GFP expression in various floral structures.

In order to demonstrate the selection of tolerant shoots containing a linked gene, a plant expressible DMO-encoding nucleic acid coupled to a plant expressible GFP-encoding nucleic and introduced into cells following selection. The cultures were examined for GFP expression 45 days after inoculation (DAI). GFP-positive small buds were observed on several explants, suggesting that these buds originated from cells transformed with the linked DMO-encoding polynucleotide molecule (FIG. 2). Several of these buds developed into GFP positive shoots and were positive for GFP gene (FIGS. 3, 6). These results demonstrated that a DMO-encoding polynucleotide molecule can be used as a selectable marker and be used for recovery of transformants containing and expressing a linked gene. Confirmation that the GFP transgene was inherited in the progeny was found by self-pollinating $R_0$ plants transformed with pMON73691. Immature $R_1$ seeds (about 4 mm in length) were collected and cut into two halves to expose the cotyledon tissue. GFP expression was detected in the cotyledon tissue of seeds under a dissecting microscope equipped with fluorescent light.

Rooting was also accomplished in Oasis Growing Medium i.e. plugs (Smithers-Oasis North America, Kent, Ohio, USA). A total of 102 Dicamba-selected shoots were inserted into Oasis plugs for inducing roots. The plugs were surrounded by a liquid medium containing 0.01 mg/l dicamba. The shoots in the plugs were kept in culture room at 28° C. and 16-h light. Thirty shoots developed roots and appeared to be resistant to dicamba showing relatively expanded new leaves. The plants with roots were tested by invader assay and 19 plants were found to contain both DMO and GUS genes. The escape rate on the liquid medium was about 33%, which was much lower than the 53% escape rate when the roots were induced in the semi-solid medium. The negative phenotypes of the shoots i.e., cupping leaves could be seen sooner in the liquid selection medium than in the semi-solid medium. This suggested that rooting in the liquid selection medium could be a more efficient method to eliminate escapes.

Example 3

Molecular Analysis of Transformed Soybean Plants

In order to confirm that the dicamba tolerant plants obtained were the result of transfer of DMO-encoding polynucleotides, leaf tissue was collected from each $R_0$ or $R_1$ plant, DNA was extracted, and the presence of the DMO-encoding polynucleotide was confirmed by Invader™ technology (Third Wave Technologies, Madison, Wis.) and Southern blot analysis using non-radioactive probe kit from Roche (Indianapolis, Ind.).

For the Invader assay, the primers used were: primary probe 5'-acggacgcggag ATGCTCAACTTCATCGC-3' (SEQ ID NO: 13) and Invader oligo 5'-TCCGCTGGAACA AGGT-GAGCGCGT-3' (SEQ ID NO: 14). The sequence in lower case letters in the primary probe is the 5' flap sequence which is cleaved and is not complimentary to the target sequence.

For Southern blot analysis a DNA fragment of 897 bp was used to prepare the probe. The forward primer 5'-GTCGCT-GCCCTGCTTGATATT-3' (SEQ ID NO: 15) and the reverse primer 5'-CGCCGCTTCTAGTTGTTC-3' (SEQ ID NO: 16) were used to amplify the 897 bp DNA fragment. A total of 12 rooted shoots selected on 0.01 mg/l dicamba shoots were transferred to soil. Ten plants were assayed by Invader and/or Southern analysis. Seven of these showed the presence of the DMO-encoding nucleic acid (Table 3). Several of these were also positive for GFP-encoding polynucleotides confirming the ability to use the DMO-encoding nucleic acid as a selectable marker for recovery of transformants containing a linked gene.

TABLE 3

Testing of R0 plants for DMO-encoding nucleic acid by Invader and/or Southern Analysis.

| Plant Name | Origin (Exp-Trt) | Invader | Southern |
|---|---|---|---|
| GM_A4755D | 533-1 | + | + |
| GM_A4756D | 533-1 | − | − |
| GM_A4757D | 533-1 | − | − |
| GM_A4758D | 533-1 | − | − |
| GM_A4763D | 533-1 | + | + |
| GM_A4759D | 534-1 | + | + |
| GM_A4760D | 534-1 | − | + |
| GM_A4761D | 534-1 | + | + |
| GM_A4764D | 534-1 | N/T | + |
| GM_A5087D | 534-1 | N/T | + |

Example 4

Figure 7:
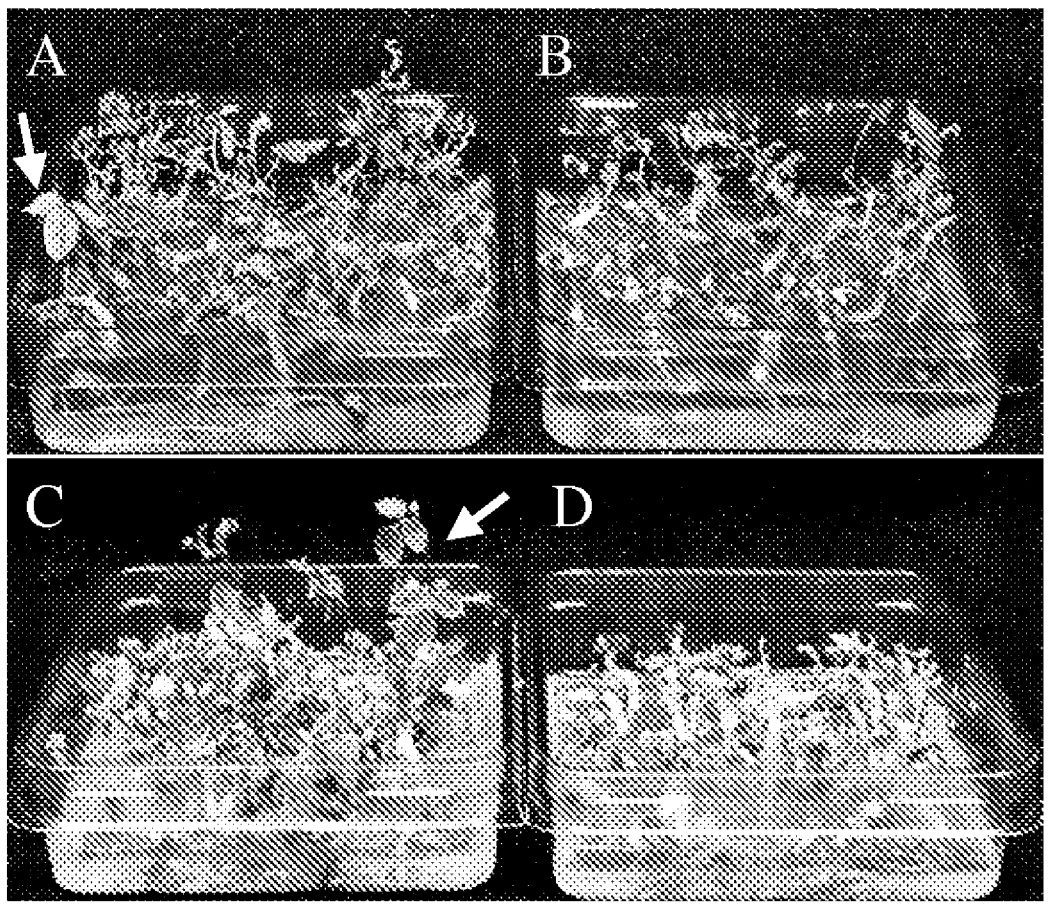
FIG. 7. Soybean explants cultured on selection medium containing 0.01 mg/l dicamba after being inoculated with Agrobacterium harboring different constructs containing different versions of DMO gene driven with different CTP. (A) pMON73696, DMO-w, with CTP1. (B and D) pMON73698, DMO-c with CTP1. (C) pMON73691, DMO-c, with CTP2. The pictures were taken 39 (A&B) and 54 DAI (C&D), respectively. Resistant shoots are shown by arrow in panels A and C.

Selection of Dicamba-Tolerant Plants Transformed with DMO-Encoding Polynucleotide Molecule Variants Two DMO-encoding polynucleotide molecule variants were used to obtain dicamba tolerant plants. The first variant had cysteine at amino acid position 112 (DMOCys$_{112}$; pMON73698) and the second had tryptophan at amino acid position 112 (DMOTrp$_{112}$; pMON73696). Selection using both variants resulted into dicamba tolerant shoots (FIG. 7). Following selection and shoot and root induction, the rooted plants were moved to soil for growing to maturity and assayed by Invader™ and/or Southern analysis for the presence of DMO-encoding nucleic acid. Several plants transformed with pMON73696 were found to be positive for the DMO gene in $R_0$ and $R_1$ generation indicating germline transformation using the method of the present invention.

TABLE 4

Selection of dicamba-tolerant shoots transformed with DMO-encoding nucleic acid variants.

| Medium | Construct | # Explants | # Tolerant shoots harvested | #Rooted shoots moved to soil | # plants with DMO gene (# plants assayed) |
|---|---|---|---|---|---|
| Liquid | 73696 (DMOTrp$_{112}$) | 1022 | 6 | 1 | 0 |
| | 73698 (DMOCys$_{112}$) | 869 | 0 | 0 | 0 |
| | 73696 (DMOTrp$_{112}$) | 1200 | 25 | 9 | 3 |
| | 73698 (DMOCys$_{112}$) | 1200 | 0 | 0 | 0 |
| Semisolid | 73696 (DMOTrp$_{112}$) | 1536 | 94 | 50 | 28 (47) |
| | 73698 (DMOCys$_{112}$) | 1845 | 3 | 0 | 0 (0) |
| | 73696 (DMOTrp$_{112}$) | 450 | 27 | 18 | 10 (16) |
| | 73698 (DMOCys$_{112}$) | 475 | 0 | 0 | 0 (0) |

Example 5

Selection of Dicamba-Tolerant Plants Transformed with DMO-Encoding Polynucleotide Molecules Combined with Different Chloroplast Transit Peptides It is known that different chloroplast transit peptides (CTPs) target a foreign polypeptide to chloroplasts with different efficiencies. The effect of different types of CTPs was therefore tested by transforming soybean explants with DMO-encoding polynucleotide molecules targeted either by CTP2 (pMON73691) or CTP1 (pMON73698) or not targeted to chloroplasts (pMON73690). As shown in Table 5, in general shoots were harvested with constructs containing either CTP2 or CTP1 (also see FIG. 7). The rooted plants were moved to soil for growing to maturity and assayed by Invader™ and/or Southern analysis for the presence of DMO-encoding nucleic acid. Several plants transformed with pMON73691 were found to be positive for the DMO gene in R$_0$ and R$_1$ generation indicating germline transformation using the method of the present invention.

Several transgenic plants carrying either a PClSV/RbcS/DMO-Wdc/Nos or PClSV/CTP2nat/DMO-Cnative/Nos expression unit were also found to be tolerant to a dicamba treatment at the rate of 1 lb/A (Clarity, BASF) at V3-4 when analysed 18 DAT in a greenhouse study.

Example 6

Use of DMO-Encoding Polynucleotide Molecule as a Selectable Marker in Combination with an Agronomic Trait Gene One beneficial use of a DMO-encoding polynucleotide molecule as a selectable marker is the recovery of transformants containing a genetically linked gene, for example, conferring an improved agronomic trait. This ability was demonstrated by transforming soybean explants with pMON58498 having 2-DNAs: a first T-DNA having a DMO-encoding polynucleotide molecule and a second T-DNA having a CP4 gene for glyphosate tolerance. Transgenic plants selected on semi-solid medium were transferred to soil and assayed by Invader™ and/or Southern analysis to show the presence of DMO and CP4 nucleic acids.

While both the DMO and CP4-encoding polynucleotide molecules could be used as a selectable marker, it was shown that transformants comprising a CP4 transgene could be selected using dicamba selection alone. As shown in Table 6, all but one regenerated plant from each of the two treatments had both DMO and CP4 genes. This study therefore demonstrates the ability to use DMO as a selectable marker for the recovery of agronomic genes. It is understood that any gene that is genetically linked to a selectable DMO marker as introduced into a genome, e.g., present within 50 cM, can be selected in this manner and that such genes need not necessarily be introduced on the same vector.

TABLE 5

Selection of dicamba tolerant plants transformed with DMO-encoding nucleic acid combined with different chloroplast transit peptides.

| Exp-Trt | Construct | # Explants | # tolerant shoots harvested | # rooted shoots moved to soil | # plant with DMO gene (# plants assayed) |
|---|---|---|---|---|---|
| 576-1 | 73691 (CTP2/DMOCys$_{112}$) | 1350 | 74 | 14 | 10 (14) |
| 625-3 | 73691 (CTP2/DMOCys$_{112}$) | 500 | 17 | 6 | 4 (5) |
| 576-2 | 73698 (CTP1/DMOCys$_{112}$) | 1050 | 22 | 1 | 1 (1) |
| 625-1 | 73690 (DMOCys$_{112}$) | 531 | 1 | 0 | 0 |
| 625-2 | 73690 (DMOCys$_{112}$) | 531 | 2 | 0 | 0 |

TABLE 6

Use of DMO as a selectable marker in combination with an agronomic trait gene.

| Exp-Trt | BAP in delay medium (mg/l) | # Explants | # tolerant shoots harvested | # shoots rooted in soil | # plants with DMO gene (# plants assayed) | # plants with CP4 gene (# plants assayed) |
|---|---|---|---|---|---|---|
| 566-1 & 567-1 | 1 | 1654 | 51 | 37 | 19 (37) | 18 (37) |
| 566-2 & 567-2 | 5 | 1800 | 35 | 11 | 3 (11) | 2 (11) |

Example 7

Tolerance of Plants Containing DMO-Encoding Polynucleotide Molecule to Other Auxin-Like Herbicides An analysis was carried out to determine whether soybean plants having DMO-encoding polynucleotide could deactivate other auxin-like herbicides in addition to dicamba. This was carried out by applying various concentrations of commercially available formulations of other auxin-like herbicides such as 2,4-D (Helena, Collierville, Tenn.), MCPA (Agriliance, St. Paul, Minn.), triclopyr (GARLON 3A; Dow Elanco, Indianapolis, Ind.), clopyralid (STINGER; Dow Elanco, Indianapolis, Ind.), picloram (TORDON 22K; Dow Elanco, Indianapolis, Ind.), or Banvel or Clarity (BASF, Raleigh, N.C.) to DMO containing plant tissues or plants.

Transgenic soybean plants were obtained by *Agrobacterium*-mediated transformation of soybean explants with a DMO-encoding polynucleotide as described above for the events designated Events 1-4. A non-transgenic line was used as a control. Non-transgenic and transgenic soybean seeds were planted into 3,5-inch square plastic pots containing Redi-earth™ (Scotts-Sierra Horticultural Products Co., Marysville, Ohio). The pots were placed on capillary matting in 35 inch×60 inch fiberglass watering trays for overhead and/or sub-irrigation for the duration of the test period so as to maintain optimum soil moisture for plant growth. The pots were fertilized with Osmocote (14-14-14 slow release; Scotts-Sierra Horticultural Products Co., Marysville, Ohio) at the rate of 100 gm/cu.ft. to sustain plant growth for the duration of greenhouse trials. The plants were grown in greenhouses at 27°/21° C. day/night temperature, with relative humidity between 25%-75% to simulate warm season growing conditions of late spring. A 14 h minimum photoperiod was provided with supplemental light at about 600 µE as needed.

All herbicide applications were made with the track sprayer using a Teejet 9501E flat fan nozzle (Spraying Systems Co, Wheaton, Ill.) with air pressure set at a minimum of 24 psi (165 kpa). The spray nozzle was kept at a height of about 16 inches above the top of plant material for spraying. The spray volume was 10 gallons per acre or 93 liters per hectare. Applications were made when plants had reached V-3 stage. All trials were established in a randomized block design (randomized by rate) with 4 to 6 replications of each treatment depending on plant quality, availability and to account for any environmental variability that may have occurred within the confines of each greenhouse.

All treated plants in greenhouse trials were visually assessed at about 4, 14, 18, and 21 days after treatment (DAT) for injury on a scale of 0 to 100 percent relative to untreated control plants, with zero representing "no" injury and 100% representing "complete" injury or death. Data were collected using a palm top computer and analyzed using standard statistical methods. The results shown in Table 9 clearly indicate tolerance of transgenic soybean to other auxin-like herbicides such as 2,4-D and MCPA relative to the non-transgenic line.

TABLE 7

Percentage injury relative to un-treated controls at 25 DAT post-V3 applications of different auxin-like herbicides to non-transgenic or transgenic soybean plants.*

| Herbicide | Plant/trial | 280 | 561 | 1120 |
|---|---|---|---|---|
| | | % injury at shown rates (g ae/ha**) at 21 DAT | | |
| Dicamba (Clarity) | Non-transgenic | | 100 | 100 |
| | Event 1 | | 0.0 | 1.2 |
| | Event 2 | | 0.0 | 1.7 |
| | Event 3 | | 0.0 | 0.7 |
| | Event 4 | | 0.0 | 1.5 |
| Dicamba (Banvel) | Non-transgenic | | 100.0 | 100.0 |
| | Event 1 | | 0.0 | 1.5 |
| | Event 2 | | 0.0 | 0.7 |
| | Event 3 | | 0.0 | 0.5 |
| | Event 4 | | 0.0 | 1.3 |
| 2,4-D | Non-transgenic | 86.8 | 100.0 | 100.0 |
| | Event 1 | 58.3 | 75.0 | 100.0 |
| | Event 2 | 64.2 | 94.7 | 100.0 |
| | Event 3 | 40.0 | 85.0 | 100.0 |
| | Event 4 | 45.8 | 84.2 | 100.0 |
| MCPA | Non-transgenic | 93.0 | 98.3 | 100.0 |
| | Event 1 | 72.5 | 99.3 | 100.0 |
| | Event 2 | 55.0 | 95.0 | 99.7 |
| | Event 3 | 55.0 | 95.8 | 100.0 |
| | Event 4 | 88.3 | 98.8 | 100.0 |
| | LSD | 16.3 | 10.6 | 3.7 |
| | | % injury shown rates (g ae/ha**) at 14 DAT | | |
| Triclopyr | Non-transgenic | 86.7 | 97.3 | 98.7 |
| | Event 1 | 88.3 | 95.7 | 99.3 |
| | Event 2 | 86.7 | 98.7 | 99.3 |
| | Event 3 | 86.7 | 94.0 | 96.3 |
| | Event 4 | 90.8 | 98.0 | 99.2 |
| Clopyralid | Non-transgenic | 99.3 | 100.0 | 100.0 |
| | Event 1 | 99.2 | 100.0 | 100.0 |
| | Event 2 | 98.2 | 99.7 | 100.0 |
| | Event 3 | 99.3 | 100.0 | 100.0 |
| | Event 4 | 99.7 | 100.0 | 100.0 |
| Picloram | Non-transgenic | 99.3 | 100.0 | 100.0 |
| | Event 1 | 99.7 | 100.0 | 100.0 |
| | Event 2 | 99.3 | 100.0 | 100.0 |
| | Event 3 | 99.3 | 99.7 | 100.0 |
| | Event 4 | 99.3 | 100.0 | 100.0 |
| | LSD | 2.9 | 1.8 | 1.4 |

*The % injury was represented as ANOVA mean comparisons.
**grams of active acid equivalent/hectare This example shows that transgenic soybean plants exhibit tolerance to other auxin-like herbicides, indicating a likely common deactivation mechanism for dicamba and other auxin-like herbicides such as 2,4-D and MCPA. In case of triclopyr, chlopyralid, and picloram, the application rate of 280 g ae/ha appeared too stringent in this study and thus lower concentrations may be desired in a most settings to reduce plant damage. The results indicate that auxin-like herbicides may be used for selecting plant cells transformed with DMO-encoding polynucleotide molecules, especially in case of plants that are very sensitive to dicamba, for example, cotton. The appropriate concentration of the auxin-like herbicide for selection under a given set of conditions may be optimized using a test grid of treatments followed by observation of treated plant tissues. An example of such a grid analyzes the effect of concentrations of from about 0.001 mg/l to about 10 mg/l, including 0.01, 0.1, 1.0, 2.0, and 5.0 mg/L.

Another auxin-like herbicide Butyrac 200 (2,4-DB; Albaugh) was also tested on transgenic soybean plants carrying a DMO gene for testing the plants tolerance to it. The herbicide was applied as a post-emergence treatment at three application rates on two transgenic soybean events and compared with a non-transgenic line for total crop injury across all three application rates: 280 g/ha (0.25 lb/a), 561 g/ha (0.5 lb/a) and 841 g/ha (0.75 lb/a) (see Table 8). Both transgenic soybean lines showed low level of tolerance to 2,4-DB. This example demonstrates that dicamba tolerant soybean is also tolerant to low levels of 2,4-DB and should be useful in managing damage from spray drift from the same or neighboring fields to prevent crop loses, and would exhibit tolerance to residual levels of 2,4-DB following incomplete washing of herbicide delivery equipment.

TABLE 8

Percentage injury relative to the untreated control at 16 DAT by the application of 2,4-DB to non-transgenic or transgenic soybean plants.

| Herbicide | Plant | % injury at shown rates (g ae/ha) at 16 DAT | | |
|---|---|---|---|---|
| | | 280 | 561 | 1120 |
| 2,4-DB (Butyrac 200) | Non-transgenic NE3001 | 59.2 | 70.0 | 79.2 |
| | 462-1-21 | 25.0 | 43.3 | 75.8 |
| | 469-13-19 | 18.3 | 37.5 | 70.0 |

Example 8

Use of DMO Gene as a Selectable Marker Against Other Auxin-Like Herbicides

Freshly isolated soybean explants (mature embryo axes without cotyledons) were inoculated with *Agrobacterium* strain ABI harboring pMON73691 (containing DMO and GFP genes). After 3-d co-culture with *Agrobacterium* at 23° C. and a photoperiod of 16-h light and 8-h dark, the explants were cultured in liquid delay medium which contained modified woody plant medium supplemented with 5 mg/l BAP, 200 mg/l carbenicillin, 200 mg/l cefotaxime and 100 mg/l ticarcillin. The explants were in the delay medium for 4 days. They were then transferred to liquid selection medium in PLANTCONs. The selection medium was the same as the delay medium except of addition of various levels of 2,4-D (0.01, 0.1, 1.0 or 2.0 mg/L) or 0.01 mg/L dicamba as shown in Table 9 below. Each PLANTCON contained 60 ml of the selection medium and one piece of foam sponge with 5 slits. Twenty-five explants were evenly inserted into the slits. The cultures were maintained at 28° C. and a photoperiod of 16-h light and 8-h dark, and were examined periodically under a sterile microscope equipped for detecting GFP expressing tissues. At 48 days after inoculation (DAI), GFP-expressing (GFP+) buds or young shoots were observed on number of explants in the treatments with 0.01 mg/L dicamba, 0.01, 0.1 or 1.0 mg/L 2,4-D, but not on the explants treated with 2 mg/L 2,4-D. Extensive callus development was observed on the explants in treatments with 1 or 2 mg/L 2,4-D. In the treatment with 0.01 or 0.1 mg/L 2,4-D, the explants had extensive shoot growth, and a few had elongated GFP+ shoots.

TABLE 9

Summary of experiment using DMO as a selectable marker and 2,4-D as the selective agent.

| Treatment # | Selective agent and concentration | # Explants inoculated | # Explants w/GFP+ buds/young shoots at 48DAI |
|---|---|---|---|
| 710-1 | 0.01 mg/L dicamba (control) | 375 | 28 |
| 710-2 | 0.01 mg/L 2,4-D | 375 | 33 |
| 710-3 | 0.1 mg/L 2,4-D | 375 | 19 |
| 710-4 | 1 mg/L 2,4-D | 375 | 4 |
| 710-5 | 2 mg/L 2,4-D | 375 | 0 |

Example 9

Selection of Dicamba-Tolerant Plants Transformed with DMO-Encoding Polynucleotide without a Delay Step Transgenic plants with a DMO gene without a delay-to-selection step were produced in three studies. As an example, explants were infected and co-cultivated with *Agrobacterium* harboring pMON73696. After the co-culture period, the explants were cultured on liquid medium containing 5 mg/l BAP and 0.01 mg/l dicamba for 4 day, and then transferred onto to the liquid or semi-solid selection medium with 0.01 mg/l dicamba. As shown in Table 10, dicamba tolerant shoots could be obtained from the treatments (717-2 and 757-2) that utilized selection immediately after co-culture with *Agrobacterium*.

TABLE 10

Selection of dicamba-tolerant plants transformed with DMO-encoding polynucleotide without a delay step.

| Experimental Treatment | Number of days delayed to selection | Construct (pMON) | # Explants | # Plants moved to soil | # Plants assayed w/ Invader | # Plants w/ the gene |
|---|---|---|---|---|---|---|
| 717-1 | 4 | 73696 | 608 | 15 | 15 | 4 |
| 717-2 | 0 | 73696 | 665 | 14 | 12 | 6 |
| 757-1 | 4 | 73696 | 542 | 13 | 11 | 6 |
| 757-2 | 0 | 73696 | 542 | 7 | 7 | 7 |

Example 10

Use of DMO as a Selectable Marker for *Arabidopsis*

Figure 8:
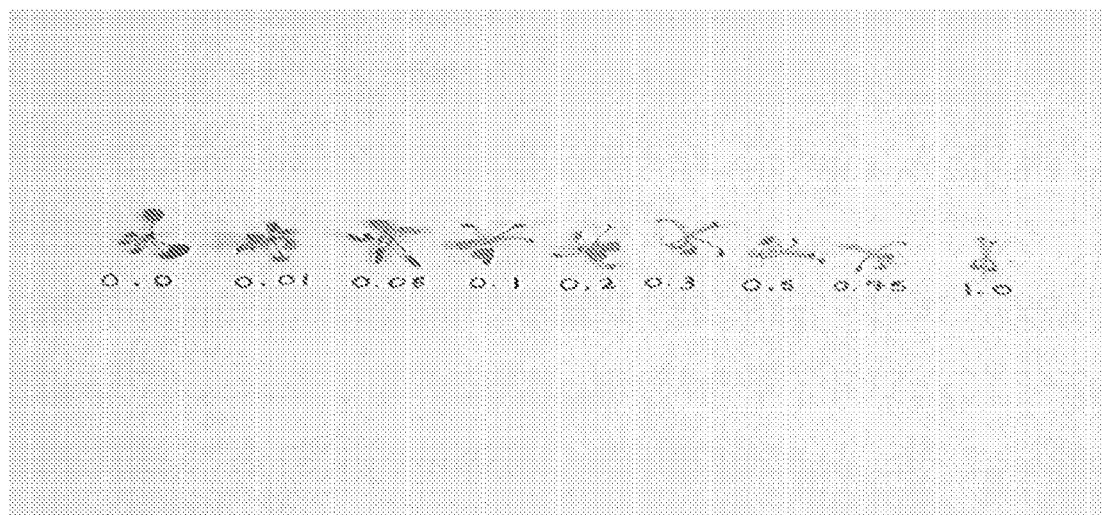
FIG. 8. Shows susceptibility of wild type *Arabidopsis* to various concentration of dicamba in culture medium.
Figure 9:
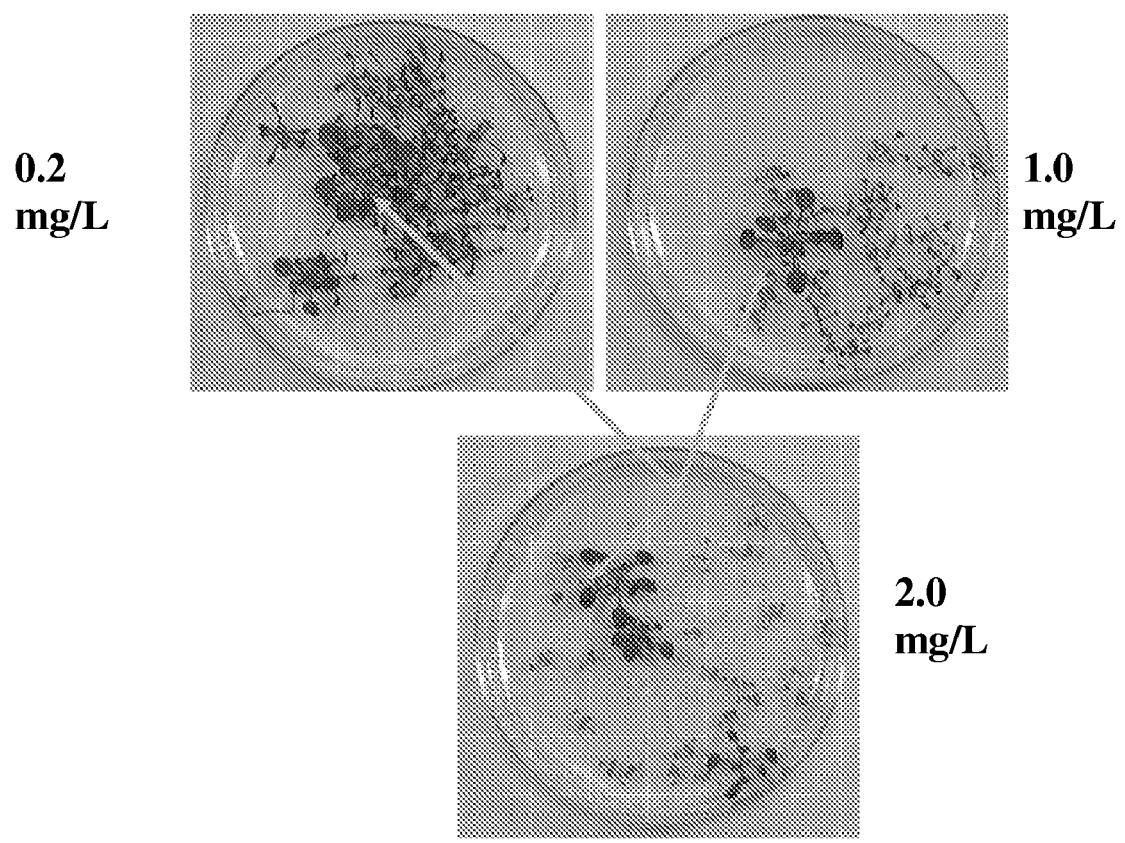
FIG. 9. Shows recovery of dicamba tolerant *Arabidopsis* plants transformed with a DMO-encoding polynucleotide.

The susceptibility of *Arabidopsis* to different levels of dicamba was first tested. Wild type *Arabidopsis* var. Columbia seeds were plated on plant tissue culture medium containing various levels of dicamba. FIG. 8 shows that wild type *Arabidopsis* was quite susceptible to 1.0 mg/L in the culture medium. *Arabidopsis* plants were then transformed with the constructs containing DMO polynucleotides using the floral dip method (Clough and Bent, 1998). $R_1$ seeds were plated on the culture medium containing up to 4 mg/L of dicamba. FIG. 9, for example, shows recovery of dicamba tolerant plants (shown by arrows) after transformation with pMON 73696. These dicamba tolerant plants were found to contain one or more copies of DMO nucleotide as ascertained by the Invader™ test. The example demonstrated the utility of DMO gene in producing dicamba tolerant plants of other plant species.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,554,101; U.S. Pat. No. 4,940,838; U.S. Pat. No. 5,017,692; U.S. Pat. No. 5,229,114; U.S. Pat. No. 5,302,523; U.S. Pat. No. 5,304,730; U.S. Pat. No. 5,322,938; U.S. Pat. No. 5,352,605; U.S. Pat. No. 5,359,142; U.S. Pat. No. 5,362,865; U.S. Pat. No. 5,384,253; U.S. Pat. No. 5,445,962; U.S. Pat. No. 5,463,175; U.S. Pat. No. 5,464,763; U.S. Pat. No. 5,464,765; U.S. Pat. No. 5,491,084; U.S. Pat. No. 5,512,466; U.S. Pat. No. 5,516,671; U.S. Pat. No. 5,530,196; U.S. Pat. No. 5,538,877; U.S. Pat. No. 5,538,880; U.S. Pat. No. 5,543,576; U.S. Pat. No. 5,545,818; U.S. Pat. No. 5,550,318; U.S. Pat. No. 5,552,299; U.S. Pat. No. 5,563,055; U.S. Pat. No. 5,567,600; U.S. Pat. No. 5,567,862; U.S. Pat. No. 5,591,616; U.S. Pat. No. 5,608,149; U.S. Pat. No. 5,633,435; U.S. Pat. No. 5,641,876; U.S. Pat. No. 5,659,122; U.S. Pat. No. 5,689,041; U.S. Pat. No. 5,689,052; U.S. Pat. No. 5,716,837; U.S. Pat. No. 5,750,876; U.S. Pat. No. 5,763,241; U.S. Pat. No. 5,763,245; U.S. Pat. No. 5,773,696; U.S. Pat. No. 5,804,425; U.S. Pat. No. 5,837,848; U.S. Pat. No. 5,850,019; U.S. Pat. No. 5,850,023; U.S. Pat. No. 5,866,775; U.S. Pat. No. 5,869,720; U.S. Pat. No. 5,880,275; U.S. Pat. No. 5,942,658; U.S. Pat. No. 5,942,664; U.S. Pat. No. 5,958,745; U.S. Pat. No. 5,959,091; U.S. Pat. No. 5,981,834; U.S. Pat. No. 5,985,605; U.S. Pat. No. 5,998,700; U.S. Pat. No. 6,011,199; U.S. Pat. No. 6,013,864; U.S. Pat. No. 6,015,940; U.S. Pat. No. 6,023,013; U.S. Pat. No. 6,051,753; U.S. Pat. No. 6,063,597; U.S. Pat. No. 6,063,756; U.S. Pat. No. 6,072,103; U.S. Pat. No. 6,080,560; U.S. Pat. No. 6,093,695; U.S. Pat. No. 6,107,549; U.S. Pat. No. 6,110,464; U.S. Pat. No. 6,121,436; U.S. Pat. No. 6,140,075; U.S. Pat. No. 6,140,078; U.S. Pat. No. 6,146,826; U.S. Pat. No. 6,153,814; U.S. Pat. No. 6,156,573; U.S. Pat. No. 6,166,292; U.S. Pat. No. 6,171,640; U.S. Pat. No. 6,175,060; U.S. Pat. No. 6,177,611; U.S. Pat. No. 6,177,615; U.S. Pat. No. 6,215,048; U.S. Pat. No. 6,221,649; U.S. Pat. No. 6,222,098; U.S. Pat. No. 6,225,114; U.S. Pat. No. 6,228,623; U.S. Pat. No. 6,228,992; U.S. Pat. No. 6,232,526; U.S. Pat. No. 6,235,971; U.S. Pat. No. 6,242,241; U.S. Pat. No. 6,248,536; U.S. Pat. No. 6,248,876; U.S. Pat. No. 6,252,138; U.S. Pat. No. 6,271,443; U.S. Pat. No. 6,281,016; U.S. Pat. No. 6,284,949; U.S. Pat. No. 6,294,714; U.S. Pat. No. 6,313,378; U.S. Pat. No. 6,316,407; U.S. Pat. No. 6,326,351; U.S. Pat. No. 6,372,211; U.S. Pat. No. 6,380,462; U.S. Pat. No. 6,380,466; U.S. Pat. No. 6,399,330; U.S. Pat. No. 6,423,828; U.S. Pat. No. 6,426,446; U.S. Pat. No. 6,426,447; U.S. Pat. No. 6,429,357; U.S. Pat. No. 6,429,362; U.S. Pat. No. 6,433,252; U.S. Pat. No. 6,437,217; U.S. Pat. No. 6,441,277; U.S. Pat. No. 6,444,876; U.S. Pat. No. 6,448,476; U.S. Pat. No. 6,459,018; U.S. Pat. No. 6,468,523; U.S. Pat. No. 6,476,295; U.S. Pat. No. 6,483,008; U.S. Pat. No. 6,489,461; U.S. Pat. No. 6,495,739; U.S. Pat. No. 6,501,009; U.S. Pat. No. 6,506,962; U.S. Pat. No. 6,518,488; U.S. Pat. No. 6,521,442; U.S. Pat. No. 6,531,648; U.S. Pat. No. 6,537,750; U.S. Pat. No. 6,537,756; U.S. Pat. No. 6,538,109; U.S. Pat. No. 6,538,178; U.S. Pat. No. 6,538,179; U.S. Pat. No. 6,538,181; U.S. Pat. No. 6,541,259; U.S. Pat. No. 6,555,655; U.S. Pat. No. 6,573,361; U.S. Pat. No. 6,576,818; U.S. Pat. No. 6,589,767; U.S. Pat. No. 6,593,293; U.S. Pat. No. 6,596,538; U.S. Pat. No. 6,608,241; U.S. Pat. No. 6,617,496; U.S. Pat. No. 6,620,988; U.S. Pat. No. 6,635,806; U.S. Pat. No. 6,639,054; U.S. Pat. No. 6,642,030; U.S. Pat. No. 6,645,497; U.S. Pat. No. 6,653,280; U.S. Pat. No. 6,653,530; U.S. Pat. No. 6,657,046; U.S. Pat. No. 6,660,849; U.S. Pat. No. 6,663,906; U.S. Pat. No. 6,686,452; U.S. Pat. No. 6,706,950; U.S. Pat. No. 6,713,063; U.S. Pat. No. 6,716,474; U.S. Pat. No. 6,723,837; U.S. Pat. No. 6,723,897; U.S. Pat. No. 6,770,465; U.S. Pat. No. 6,774,283; U.S. Pat. No. 6,803,501; U.S. Pat. No. 6,809,078; U.S. Pat. No. 6,812,379; U.S. Pat. No. 6,822,141; U.S. Pat. No. 6,828,475

U.S. Provisional Appln. Ser. No. 60/891,675

U.S. Patent Pub. 2005/0005321; U.S. Patent Pub. 2003/0115626; U.S. Patent Pub. 2003/01403641; U.S. Patent Pub. 2003/0135879; U.S. Patent Pub. 2003/0028917

U.S. patent application Ser. No. 09/757,089; U.S. patent application Ser. No. 11/749,583

U.S. Pat. RE37,543

U.S. Pat. RE38,446

Becker et al., *Plant Mol. Biol.*, 20:49, 1992.

Bevan et al., *NAR*, 11: 369, 1983.

Broothaerts et al, *Nature*, 433: 629-633, 2005.

Carrington and Freed, *J. Virology*, 64:1590, 1990.

Chalfie et al., *Science*, 263:802, 1994.

Chandler et al., *Plant Cell*, 1:1175-1183, 1989.

Charest et al., *Plant Cell Rep.*, 8:643, 1990.

Chu et al., *Scientia Sinica*, 18:659, 1975.

Clough and Bent, *Plant J.*, 16:735, 1998.

Comai et al., *Nature*, 317:741, 1985.

Cork and Khalil, *Adv. Appl. Microbiol.*, 40: 289, 1995.

Cork and Krueger, *Adv. Appl. Microbiol.*, 38:1, 1991.

Coruzzi et al., *EMBO J.*, 3: 1671, 1984.
Creissen et al., *Plant J.*, 2:129, 1991.
Crop Protection Reference, Chemical & Pharmaceutical Press, Inc., NY, 11th Ed., 1803-1821,
De Block et al., *EMBO J.*, 3:1681, 1984.
De Block et al., *EMBO J.*, 6:2513, 1987.
della-Cioppa et al., *Proc. Natl. Acad. Sci. USA*, 83:6873-6877, 1986.
Depicker et al, *J. Mol. Appl. Genet.*, 1: 561, 1982.
Duncan et al., *Planta*, 165:322, 1985.
Ebert et al., *Proc. Natl. Acad. Sci. USA*, 84:5745-5749, 1987.
Eckes et al., *Mol. Gen. Genet.*, 205:14, 1986.
Eichholtz et al., *Somatic Cell Mol. Genet.*, 13:67, 1987.
EP Appln. 553494
EP Appln. 646643
Fraley et al., *Proc. Natl. Acad. Sci. USA*, 80:4803, 1983.
Gamborg et al., *Exp. Cell Res.*, 50:151, 1968.
Gordon-Kamm et al., *Plant Cell*, 2:603, 1990.
Haseloff et al., *TIG*, 11:328-329, 1995.
Hayford et al., *Plant Physiol.*, 86:1216, 1988.
Hille et al., *Plant Mol. Biol.*, 7:171, 1986.
Horsch et al., *Science*, 227:1229, 1985.
Ingelbrecht et al., *Plant Cell*, 1:671, 1989.
Jefferson, *Plant Mol. Biol. Rep.*, 5:387, 1987.
Jones et al., *Mol. Gen. Genet.*, 210:86, 1987.
Kado, *Crit. Rev. Plant. Sci.*, 10:1, 1991.
Klee et al., *Mol. Gen. Genet.*, 210:437-442, 1987.
Koncz et al., *Proc. Natl. Acad. Sci., USA*, 84:131, 1987.
Krueger et al., *J. Agric. Food Chem.*, 37:534, 1989.
Kyte and Doolittle, *J. Mol. Biol.*, 157(1):105-132, 1982.
Lawton et al., *Plant Mol. Biol.*, 9:315-324, 1987.
Linsmaier and Skoog, *Physio. Plant*, 18:100, 1965.
Lloyd and McCown, *Proc. Int. Plant Prop. Soc.*, 30:421, 1981.
Maniatis, et al., Molecular Cloning, A Laboratory Manual, Cold Spring Harbor Press, Cold Spring Harbor, N.Y., 1982.
McCown and Lloyd, *Hort. Science*, 16:453, 1981.
Miki et al., In: *Methods in Plant Molecular Biology and Biotechnology*, Glick and Thompson (Eds.), CRC Press, 67-88, 1993.
Moloney et al., *Plant Cell Reports*, 8:238, 1989.
Murashige and Skoog, *Physiol. Plant*, 15:473-497, 1962.
Nitsch and Nitsch, *Science*, 163:85, 1969.
Odell et al., *Nature*, 313:810-812, 1985.
PCT Appln. WO 97/11086
PCT Appln. WO 95/24492
PCT Appln. WO 97/31115
PCT Appln. WO 97/41228
Rojiyaa et al., 1987 (JP 1987201527-A), GenBank Accession E01312.
Sambrook et al., In: *Molecular cloning: a laboratory manual*, 2nd Ed., Cold Spring Harbor Laboratory Press, Cold Spring Harbor, N.Y., 1989.
Schenk and Hildebrandt, *Can. J. Bot.*, 50:199, 1972.
Shah et al., *Science*, 233:478, 1986.
Southern, *Mol. Biol.*, 98:503, 1975.
Stalker et al., *Science*, 242:419, 1988.
Streber and Willmitzer, *Bio/Technology*, 7:811, 1989.
Svab et al., *Plant Mol. Biol.*, 14:197, 1990.
Teeri et al., *EMBO J.*, 8:343, 1989.
Turner and Foster, *Molec. Biotechn.*, 3:225, 1995.
Uchimiya and Murashige, *Plant Physiol.*, 15:473, 1962.
Vanden Elzen et al., *Plant Mol. Biol.*, 5:299, 1985.
Walker et al., *Proc. Natl. Acad. Sci. USA*, 84:6624-6628, 1987.
Yang et al., *Proc. Natl. Acad. Sci. USA*, 87:4144-4148, 1990.

---

What is claimed is:

1. A method for selecting a transformed soybean plant cell comprising the steps of:
   a) contacting a population of plant cells comprising a transgenic soybean plant cell transformed with a polynucleotide encoding dicamba monooxygenase with medium comprising auxin-like herbicide in an amount that inhibits the growth of cells from the population lacking the polynucleotide, wherein the polynucleotide comprises a nucleic acid sequence selected from: (1) a nucleic acid sequence encoding the polypeptide of SEQ ID NO: 6, (2) a nucleic acid sequence comprising the sequence of SEQ ID NO: 5, and (3) a nucleic acid sequence encoding a polypeptide with at least 90% sequence identity to the polypeptide of SEQ ID NO:6, wherein the polypeptide has dicamba monooxygenase activity; and
   b) selecting the transformed soybean plant cell from the population of plant cells based on tolerance exhibited by the transformed cell to the auxin-like herbicide further wherein:
   said polynucleotide encoding dicamba monooxygenase is operatively linked to a chloroplast transit peptide coding sequence.

2. The method of claim 1, comprising culturing the population of plant cells on a medium lacking the auxin-like herbicide prior to step a) and/or between step a) and step b).

3. The method of claim 2, wherein the medium lacking the auxin-like herbicide contains a cytokinin.

4. The method of claim 2, wherein the medium lacking the auxin-like herbicide contains 6-benzyl amino purine (BAP).

5. The method of claim 4, wherein the 6-benzyl amino purine is in a concentration of about 10 mg/l of medium or less.

6. The method of claim 1, wherein the polynucleotide encoding dicamba monooxygenase is not genetically linked to a selectable or screenable marker gene other than dicamba monooxygenase.

7. The method of claim 1, further comprising the step of:
   c) regenerating a fertile transgenic soybean plant from the transformed soybean plant cell.

8. The method of claim 1, wherein the medium contains at least two auxin-like herbicides.

9. The method of claim 8, wherein the medium contains dicamba and 2,4-dichlorophenoxyacetic acid.

10. The method of claim 1, wherein the population of cells comprises a cotyledon explant.

11. The method of claim 10, wherein the transformed plant cell is prepared by *Agrobacterium*-mediated transformation.

12. The method of claim 1, wherein said auxin-like herbicide comprises 2,4-D, MCPA or 2,4-DB.

13. The method of claim 1, wherein said auxin-like herbicide comprises dicamba in a concentration of from about 0.001 mg/L to about 0.02 mg/L.

* * * * *

SEQUENCE LISTING

```
<160> NUMBER OF SEQ ID NOS: 29

<210> SEQ ID NO 1
<211> LENGTH: 1023
<212> TYPE: DNA
<213> ORGANISM: Artificial
<220> FEATURE:
<223> OTHER INFORMATION: Based on dicamba monooxygenase gene from
      Pseudomonas maltophilia

<400> SEQUENCE: 1
atggccactt tcgttagaaa cgcttggtac gttgctgcac ttcctgagga gttgagcgag        60
aagcctctag gaagaactat cctcgatact ccactagctc tctatcgtca acctgacgga       120
gttgtcgctg ccctgcttga tatttgtccg catcgcttcg ctccgttgag tgacggtatt       180
ctagtcaacg gacatctcca gtgtccatat cacggtctga aatttgacgg aggtggccag       240
tgtgtccaca acccgcacgg caacggagcc cgccctgctt ctctgaacgt gcgatcattc       300
cctgtcgtgg aaagagacgc attgatctgg atctgccctg gagatccagc actcgcagat       360
cccggtgcta tccctgactt tgggtgtcgt gttgatccag cttaccgtac tgtcggaggt       420
tacggtcacg tggactgcaa ctacaagctc cttgtggata acctcatgga tcttggacac       480
gctcagtacg tgcaccgcgc taacgcccaa acagacgcct tcgatagact tgagcgtgag       540
gtgatcgttg gcgacggcga gatccaggcg ctcatgaaga tccctggtgg cacaccctca       600
```

-continued

```
gttctcatgg ctaagttctt gcgtggtgct aacacaccag ttgacgcctg gaacgcacatc    660 cggtggaata aggtgtcggc tatgctgaac ttcatcgcgg tcgcgccgga agggacgccg    720
aaggagcagt caatccactc ccgaggaacc catatcctta ctcctgagac cgaggcaagc    780
tgccattact tcttcggtag ttcccgcaac ttcggtatac gatccaga gatggacggt    840 gttctcagga gctggcaagc tcaagccctg gtgaaggagg acaaagtggt cgttgaagct    900
atcgaaaggc ggagggctta cgtcgaagcg aacgggatca gacccgccat gttgtcctgc    960
gacgaggcag ccgtcagggt atccaggag attgagaagc tcgaacaact agaagcggcg   1020
tga                                                                 1023
```

<210> SEQ ID NO 2
<211> LENGTH: 340
<212> TYPE: PRT
<213> ORGANISM: Artificial
<220> FEATURE:
<223> OTHER INFORMATION: Based on dicamba monooxygenase gene from
      Pseudomonas maltophilia

<400> SEQUENCE: 2

```
Met Ala Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Cys
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
```

```
            275                 280                 285
Ala Leu Val Lys Glu Asp Lys Val Val Glu Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
        340

<210> SEQ ID NO 3
<211> LENGTH: 1023
<212> TYPE: DNA
<213> ORGANISM: Artificial
<220> FEATURE:
<223> OTHER INFORMATION: Based on dicamba monooxygenase gene from
      Pseudomonas maltophilia

<400> SEQUENCE: 3
atgctcactt tcgttagaaa cgcttggtac gttgctgcac ttcctgagga gttgagcgag     60
aagcctctag gaagaactat cctcgatact ccactagctc tctatcgtca acctgacgga    120
gttgtcgctg ccctgcttga tatttgtccg catcgcttcg ctccgttgag tgacggtatt    180
ctagtcaacg gacatctcca gtgtccatat acggtctggg aatttgacgg aggtggccag    240
tgtgtccaca acccgcacgg caacggagcc cgccctgctt ctctgaacgt gcgatcattc    300
cctgtcgtgg aaagagacgc attgatctgg atctgccctg agatccagc actcgcagat    360 cccggtgcta tccctgactt tgggtgtcgt gttgatccag cttaccgtac tgtcggaggt    420
tacggtcacg tggactgcaa ctacaagctc cttgtggata acctcatgga tcttggacac    480
gctcagtacg tgcaccgcgc taacgcccaa acagacgcct tcgatagact tgagcgtgag    540
gtgatcgttg gcgacggcga gatccaggcg ctcatgaaga tccctggtgg cacaccctca    600
gttctcatgg ctaagttctt gcgtggtgct aacacaccag ttgacgcctg aacgacatc    660 cggtggaata aggtgtcggc tatgctgaac ttcatcgcgg tcgcgccgga agggacgccg    720
aaggagcagt caatccactc ccgaggaacc catatcctta ctcctgagac cgaggcaagc    780
tgccattact tcttcggtag ttcccgcaac ttcggtatag acgatccaga gatgacggt    840 gttctcagga gctggcaagc tcaagccctg gtgaaggagg acaaagtggt cgttgaagct    900
atcgaaaggc ggagggctta cgtcgaagcg aacgggatca gacccgccat gttgtcctgc    960
gacgaggcag ccgtcagggt atccaggag attgagaagc tcgaacaact agaagcggcg   1020
tga                                                                1023

<210> SEQ ID NO 4
<211> LENGTH: 340
<212> TYPE: PRT
<213> ORGANISM: Artificial
<220> FEATURE:
<223> OTHER INFORMATION: Based on dicamba monooxygenase gene from
      Pseudomonas maltophilia

<400> SEQUENCE: 4

Met Leu Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
```

```
                35                  40                  45
Cys Pro His Arg Phe Ala Pro Leu Ser Asp Gly Ile Leu Val Asn Gly
 50                  55                  60

His Leu Gln Cys Pro Tyr His Gly Leu Glu Phe Asp Gly Gly Gly Gln
 65                  70                  75                  80

Cys Val His Asn Pro His Gly Asn Gly Ala Arg Pro Ala Ser Leu Asn
                 85                  90                  95

Val Arg Ser Phe Pro Val Val Glu Arg Asp Ala Leu Ile Trp Ile Cys
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Val Glu Ala Ile Glu Arg Arg
290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
            340

<210> SEQ ID NO 5
<211> LENGTH: 1023
<212> TYPE: DNA
<213> ORGANISM: Artificial
<220> FEATURE:
<223> OTHER INFORMATION: Based on dicamba monooxygenase gene from
      Pseudomonas maltophilia

<400> SEQUENCE: 5
atgctcactt tcgttagaaa cgcttggtac gttgctgcac ttcctgagga gttgagcgag      60
aagcctctag gaagaactat cctcgatact ccactagctc tctatcgtca acctgacgga     120
gttgtcgctg ccctgcttga tatttgtccg catcgcttcg ctccgttgag tgacggtatt     180
ctagtcaacg gacatctcca gtgtccatat acggtctgg aatttgacgg aggtggccag     240
tgtgtccaca acccgcacgg caacggagcc cgccctgctt ctctgaacgt gcgatcattc     300
```

-continued

```
cctgtcgtgg aaagagacgc attgatctgg atctggcctg gagatccagc actcgcagat    360
cccggtgcta tccctgactt tgggtgtcgt gttgatccag cttaccgtac tgtcggaggt    420
tacggtcacg tggactgcaa ctacaagctc cttgtggata acctcatgga tcttggacac    480
gctcagtacg tgcaccgcgc taacgcccaa acagacgcct cgatagact tgagcgtgag     540
gtgatcgttg gcgacggcga gatccaggcg ctcatgaaga tccctggtgg cacaccctca    600
gttctcatgg ctaagttctt gcgtggtgct aacacaccag ttgacgcctg gaacgacatc    660
cggtggaata aggtgtcggc tatgctgaac ttcatcgcgg tcgcgccgga agggacgccg    720
aaggagcagt caatccactc ccgaggaacc catatcctta ctcctgagac cgaggcaagc    780
tgccattact tcttcggtag ttcccgcaac ttcggtatag acgatccaga gatggacggt    840
gttctcagga gctggcaagc tcaagccctg gtgaaggagg acaaagtggt cgttgaagct    900
atcgaaaggc ggagggctta cgtcgaagcg aacgggatca gacccgccat gttgtcctgc    960
gacgaggcag ccgtcagggt atccaggag attgagaagc tcgaacaact agaagcggcg    1020
tga                                                                 1023
```

<210> SEQ ID NO 6
<211> LENGTH: 340
<212> TYPE: PRT
<213> ORGANISM: Artificial
<220> FEATURE:
<223> OTHER INFORMATION: Based on dicamba monooxygenase gene from
      Pseudomonas maltophilia <400> SEQUENCE: 6

```
Met Leu Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Trp
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220
```

```
Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Glu Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
        340

<210> SEQ ID NO 7
<211> LENGTH: 1023
<212> TYPE: DNA
<213> ORGANISM: Artificial
<220> FEATURE:
<223> OTHER INFORMATION: Based on dicamba monooxygenase gene from
      Pseudomonas maltophilia

<400> SEQUENCE: 7
atggccacct tcgtccgcaa tgcctggtat gtggcggcgc tgcccgagga actgtccgaa      60
aagccgctcg gccggacgat tctcgacaca ccgctcgcgc tctaccgcca gcccgacggt     120
gtggtcgcgg cgctgctcga catctgtccg caccgcttcg cgccgctgag cgacggcatc     180
ctcgtcaacg gccatctcca tgccccctat cacgggctgg aattcgatgg cggcgggcag     240
tgcgtccata acccgcacgg caatggcgcc cgcccggctt cgctcaacgt ccgctccttc     300
ccggtggtgg agcgcgacgc gctgatctgg atctgtcccg cgatccggc gctggccgat     360 cctggggcga tccccgactt cggctgccgc gtcgatcccg cctatcggac cgtcggcggc     420
tatgggcatg tcgactgcaa ctacaagctg ctggtcgaca acctgatgga cctcggccac     480
gcccaatatg tccatcgcgc caacgcccag accgacgcct tcgaccggct ggagcgcgag     540
gtgatcgtcg cgacggtga gatacaggcg ctgatgaaga ttcccggcgg cacgccgagc     600
gtgctgatgg ccaagttcct gcgcggcgcc aatacccccg tcgacgcttg gaacgacatc     660
cgctggaaca aggtgagcgc gatgctcaac ttcatcgcgg tggcgccgga aggcaccccg     720
aaggagcaga gcatccactc gcgcggtacc catatcctga ccccgagac ggaggcgagc     780 tgccattatt tcttcggctc ctcgcgcaat ttcggcatcg acgatccgga gatggacggc     840
gtgctgcgca gctggcaggc tcaggcgctg gtcaaggagg acaaggtcgt cgtcgaggcg     900
atcgagcgcc gccgcgccta tgtcgaggcg aatggcatcc gcccggcgat gctgtcgtgc     960
gacgaagccg cagtccgtgt cagccgcgag atcgagaagc ttgagcagct cgaagccgcc    1020
tga                                                                  1023

<210> SEQ ID NO 8
<211> LENGTH: 340
<212> TYPE: PRT
<213> ORGANISM: Artificial
<220> FEATURE:
<223> OTHER INFORMATION: Based on dicamba monooxygenase gene from
```

Pseudomonas maltophilia

<400> SEQUENCE: 8

```
Met Ala Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Cys
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Glu Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
        340
```

<210> SEQ ID NO 9
<211> LENGTH: 1023
<212> TYPE: DNA
<213> ORGANISM: Artificial
<220> FEATURE:
<223> OTHER INFORMATION: Based on dicamba monooxygenase gene from
      Pseudomonas maltophilia

<400> SEQUENCE: 9

```
atggccactt tcgttagaaa cgcttggtac gttgctgcac ttcctgagga gttgagcgag      60
aagcctctag gaagaactat cctcgatact ccactagctc tctatcgtca acctgacgga     120
gttgtcgctg ccctgcttga tatttgtccg catcgcttcg ctccgttgag tgacggtatt     180
ctagtcaacg gacatctcca gtgtccatat cacggtctgg aatttgacgg aggtggccag     240
tgtgtccaca acccgcacgg caacggagcc cgccctgctt ctctgaacgt gcgatcattc     300
cctgtcgtgg aaagagacgc attgatctgg atctggcctg gagatccagc actcgcagat     360
cccggtgcta tccctgactt tgggtgtcgt gttgatccag cttaccgtac tgtcggaggt     420
tacggtcacg tggactgcaa ctacaagctc cttgtggata acctcatgga tcttggacac     480
gctcagtacg tgcaccgcgc taacgcccaa acagacgcct tcgatagact tgagcgtgag     540
gtgatcgttg gcgacggcga gatccaggcg ctcatgaaga tccctggtgg cacaccctca     600
gttctcatgg ctaagttctt gcgtggtgct aacacaccag ttgacgcctg gaacgacatc     660
cggtggaata aggtgtcggc tatgctgaac ttcatcgcgg tcgcgccgga agggacgccg     720
aaggagcagt caatccactc ccgaggaacc catatcctta ctcctgagac cgaggcaagc     780
tgccattact tcttcggtag ttcccgcaac ttcggtatag acgatccaga gatggacggt     840
gttctcagga gctggcaagc tcaagccctg gtgaaggagg acaaagtggt cgttgaagct     900
atcgaaaggc ggagggctta cgtcgaagcg aacgggatca gacccgccat gttgtcctgc     960
gacgaggcag ccgtcagggt atccaggag attgagaagc tcgaacaact agaagcggcg    1020
tga                                                                  1023
```

<210> SEQ ID NO 10
<211> LENGTH: 340
<212> TYPE: PRT
<213> ORGANISM: Artificial
<220> FEATURE:
<223> OTHER INFORMATION: Based on dicamba monooxygenase gene from
      Pseudomonas maltophilia

<400> SEQUENCE: 10

```
Met Ala Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Trp
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160
```

```
Ala Gln Tyr Val His Arg Ala Asn Ala Gln Thr Asp Ala Phe Asp Arg
            165                 170                 175

Leu Glu Arg Glu Val Ile Val Gly Asp Gly Glu Ile Gln Ala Leu Met
        180                 185                 190

Lys Ile Pro Gly Gly Thr Pro Ser Val Leu Met Ala Lys Phe Leu Arg
    195                 200                 205

Gly Ala Asn Thr Pro Val Asp Ala Trp Asn Asp Ile Arg Trp Asn Lys
210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Glu Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
            340

<210> SEQ ID NO 11
<211> LENGTH: 1020
<212> TYPE: DNA
<213> ORGANISM: Pseudomonas maltophilia

<400> SEQUENCE: 11
atgaccttcg tccgcaatgc ctggtatgtg gcggcgctgc ccgaggaact gtccgaaaag      60
ccgctcggcc ggacgattct cgacacaccg ctcgcgctct accgccagcc cgacggtgtg     120
gtcgcggcgc tgctcgacat ctgtccgcac cgcttcgcgc gctgagcga cggcatcctc     180 gtcaacggcc atctccaatg cccctatcac gggctggaat cgatggcgg cgggcagtgc     240 gtccataacc cgcacggcaa tggcgcccgc ccggcttcgc tcaacgtccg ctccttcccg     300
gtggtggagc gcgacgcgct gatctggatc tggcccggcg atccggcgct ggccgatcct     360
ggggcgatcc ccgacttcgg ctgccgcgtc gatcccgcct atcggaccgt cggcggctat     420 ggcatgtcg actgcaacta caagctgctg gtcgacaacc tgatggacct cggccacgcc     480
caatatgtcc atcgcgccaa cgcccagacc gacgccttcg accggctgga gcgcgaggtg     540
atcgtcggcg acggtgagat acaggcgctg atgaagattc ccggcggcac gccgagcgtg     600
ctgatggcca agttcctgcg cggcgccaat accccgtcg acgcttggaa cgacatccgc     660
tggaacaagg tgagcgcgat gctcaacttc atcgcggtgg cgccggaagg caccccgaag     720
gagcagagca tccactcgcg cggtacccat atcctgaccc cgagacgga ggcgagctgc     780 cattatttct tcggctcctc gcgcaatttc ggcatcgacg atccggagat ggacggcgtg     840
ctgcgcagct ggcaggctca ggcgctggtc aaggaggaca aggtcgtcgt cgaggcgatc     900
gagcgccgcc gcgcctatgt cgaggcgaat ggcatccgcc cggcgatgct gtcgtgcgac     960
gaagccgcag tccgtgtcag ccgcgagatc gagaagcttg agcagctcga agccgcctga    1020
```

```
<210> SEQ ID NO 12
<211> LENGTH: 339
<212> TYPE: PRT
<213> ORGANISM: Pseudomonas maltophilia

<400> SEQUENCE: 12

Met Thr Phe Val Arg Asn Ala Trp Tyr Val Ala Ala Leu Pro Glu Glu
1               5                   10                  15

Leu Ser Glu Lys Pro Leu Gly Arg Thr Ile Leu Asp Thr Pro Leu Ala
            20                  25                  30

Leu Tyr Arg Gln Pro Asp Gly Val Val Ala Ala Leu Leu Asp Ile Cys
        35                  40                  45

Pro His Arg Phe Ala Pro Leu Ser Asp Gly Ile Leu Val Asn Gly His
    50                  55                  60

Leu Gln Cys Pro Tyr His Gly Leu Glu Phe Asp Gly Gly Gly Gln Cys
65                  70                  75                  80

Val His Asn Pro His Gly Asn Gly Ala Arg Pro Ala Ser Leu Asn Val
                85                  90                  95

Arg Ser Phe Pro Val Val Glu Arg Asp Ala Leu Ile Trp Ile Trp Pro
            100                 105                 110

Gly Asp Pro Ala Leu Ala Asp Pro Gly Ala Ile Pro Asp Phe Gly Cys
        115                 120                 125

Arg Val Asp Pro Ala Tyr Arg Thr Val Gly Gly Tyr Gly His Val Asp
    130                 135                 140

Cys Asn Tyr Lys Leu Leu Val Asp Asn Leu Met Asp Leu Gly His Ala
145                 150                 155                 160

Gln Tyr Val His Arg Ala Asn Ala Gln Thr Asp Ala Phe Asp Arg Leu
                165                 170                 175

Glu Arg Glu Val Ile Val Gly Asp Gly Glu Ile Gln Ala Leu Met Lys
            180                 185                 190

Ile Pro Gly Gly Thr Pro Ser Val Leu Met Ala Lys Phe Leu Arg Gly
        195                 200                 205

Ala Asn Thr Pro Val Asp Ala Trp Asn Asp Ile Arg Trp Asn Lys Val
    210                 215                 220

Ser Ala Met Leu Asn Phe Ile Ala Val Ala Pro Glu Gly Thr Pro Lys
225                 230                 235                 240

Glu Gln Ser Ile His Ser Arg Gly Thr His Ile Leu Thr Pro Glu Thr
                245                 250                 255

Glu Ala Ser Cys His Tyr Phe Phe Gly Ser Ser Arg Asn Phe Gly Ile
            260                 265                 270

Asp Asp Pro Glu Met Asp Gly Val Leu Arg Ser Trp Gln Ala Gln Ala
        275                 280                 285

Leu Val Lys Glu Asp Lys Val Val Glu Ala Ile Glu Arg Arg Arg
    290                 295                 300

Ala Tyr Val Glu Ala Asn Gly Ile Arg Pro Ala Met Leu Ser Cys Asp
305                 310                 315                 320

Glu Ala Ala Val Arg Val Ser Arg Glu Ile Glu Lys Leu Glu Gln Leu
                325                 330                 335

Glu Ala Ala

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence:  Synthetic
```

-continued

Primer

<400> SEQUENCE: 13
acggacgcgg agatgctcaa cttcatcgc                                                29

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 14
tccgctggaa caaggtgagc gcgt                                                     24

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 15
gtcgctgccc tgcttgatat t                                                        21

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 16
cgccgcttct agttgttc                                                            18

<210> SEQ ID NO 17
<211> LENGTH: 57
<212> TYPE: PRT
<213> ORGANISM: Pisum sativum

<400> SEQUENCE: 17

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Cys
    50                  55

<210> SEQ ID NO 18
<211> LENGTH: 85
<212> TYPE: PRT
<213> ORGANISM: Arabidopsis thaliana

<400> SEQUENCE: 18

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

```
Phe Pro Ala Thr Arg Lys Ala Asn Asn Asp Ile Thr Ser Ile Thr Ser
            35                  40                  45

Asn Gly Gly Arg Val Asn Cys Met Gln Val Trp Pro Pro Ile Glu Lys
 50                  55                  60

Lys Lys Phe Glu Thr Leu Ser Tyr Leu Pro Asp Leu Thr Asp Ser Gly
 65                  70                  75                  80

Gly Arg Val Asn Cys
                85

<210> SEQ ID NO 19
<211> LENGTH: 76
<212> TYPE: PRT
<213> ORGANISM: Arabidopsis thaliana

<400> SEQUENCE: 19

Met Ala Gln Val Ser Arg Ile Cys Asn Gly Val Gln Asn Pro Ser Leu
 1               5                  10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
 50                  55                  60

Pro Leu Lys Val Met Ser Ser Val Ser Thr Ala Cys
 65                  70                  75

<210> SEQ ID NO 20
<211> LENGTH: 76
<212> TYPE: PRT
<213> ORGANISM: Arabidopsis thaliana

<400> SEQUENCE: 20

Met Ala Gln Val Ser Arg Ile Cys Asn Gly Val Gln Asn Pro Ser Leu
 1               5                  10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
 50                  55                  60

Pro Leu Lys Val Met Ser Ser Val Ser Thr Ala Cys
 65                  70                  75

<210> SEQ ID NO 21
<211> LENGTH: 72
<212> TYPE: PRT
<213> ORGANISM: Petunia hybrida

<400> SEQUENCE: 21

Met Ala Gln Ile Asn Asn Met Ala Gln Gly Ile Gln Thr Leu Asn Pro
 1               5                  10                  15

Asn Ser Asn Phe His Lys Pro Gln Val Pro Lys Ser Ser Phe Leu
            20                  25                  30

Val Phe Gly Ser Lys Lys Leu Lys Asn Ser Ala Asn Ser Met Leu Val
            35                  40                  45

Leu Lys Lys Asp Ser Ile Phe Met Gln Lys Phe Cys Ser Phe Arg Ile
 50                  55                  60

Ser Ala Ser Val Ala Thr Ala Cys
```

<210> SEQ ID NO 22
<211> LENGTH: 69
<212> TYPE: PRT
<213> ORGANISM: Triticum aestivum

<400> SEQUENCE: 22

Met Ala Ala Leu Val Thr Ser Gln Leu Ala Thr Ser Gly Thr Val Leu
1               5                   10                  15

Ser Val Thr Asp Arg Phe Arg Arg Pro Gly Phe Gln Gly Leu Arg Pro
            20                  25                  30

Arg Asn Pro Ala Asp Ala Ala Leu Gly Met Arg Thr Val Gly Ala Ser
        35                  40                  45

Ala Ala Pro Lys Gln Ser Arg Lys Pro His Arg Phe Asp Arg Arg Cys
    50                  55                  60

Leu Ser Met Val Val
65

<210> SEQ ID NO 23
<211> LENGTH: 171
<212> TYPE: DNA
<213> ORGANISM: Pisum sativum

<400> SEQUENCE: 23
atggcttcta tgatatcctc ttccgctgtg acaacagtca gccgtgcctc tagggggcaa      60
tccgccgcaa tggctccatt cggcggcctc aaatccatga ctggattccc agtgaggaag     120
gtcaacactg acattacttc cattacaagc aatggtggaa gagtaaagtg c              171

<210> SEQ ID NO 24
<211> LENGTH: 255
<212> TYPE: DNA
<213> ORGANISM: Arabidopsis thaliana

<400> SEQUENCE: 24
atggcttcct ctatgctctc ttccgctact atggttgcct ctccggctca ggccactatg      60
gtcgctcctt tcaacggact taagtcctcc gctgccttcc agccacccg caaggctaac     120 aacgacatta cttccatcac aagcaacggc ggaagagtta actgtatgca ggtgtggcct     180
ccgattgaaa agaagaagtt tgagactctc tcttaccttc ctgaccttac cgattccggt     240
ggtcgcgtca actgc                                                     255

<210> SEQ ID NO 25
<211> LENGTH: 228
<212> TYPE: DNA
<213> ORGANISM: Arabidopsis thaliana

<400> SEQUENCE: 25
atggcgcaag ttagcagaat ctgcaatggt gtgcagaacc catctcttat ctccaatctc      60
tcgaaatcca gtcaacgcaa atctccctta tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct tctgtttcca cggcgtgc                 228

<210> SEQ ID NO 26
<211> LENGTH: 228
<212> TYPE: DNA
<213> ORGANISM: Artificial sequence
<220> FEATURE:

```
<223> OTHER INFORMATION: Description of Artificial Sequence:  Artificial
      primer

<400> SEQUENCE: 26
atggcgcaag ttagcagaat ctgcaatggt gtgcagaacc catctcttat ctccaatctc    60
tcgaaatcca gtcaacgcaa atctccctta tcggtttctc tgaagacgca gcagcatcca   120
cgagcttatc cgatttcgtc gtcgtgggga ttgaagaaga gtgggatgac gttaattggc   180
tctgagcttc gtcctcttaa ggtcatgtct tctgtttcca cggcgtgc                228

<210> SEQ ID NO 27
<211> LENGTH: 216
<212> TYPE: DNA
<213> ORGANISM: Artificial sequence
<220> FEATURE:
<223> OTHER INFORMATION: Description of Artificial Sequence:  Artificial
      primer

<400> SEQUENCE: 27
atggcccaga tcaacaacat ggcccagggc atccagaccc tgaaccctaa ctctaacttc    60
cacaagccgc aagtgcccaa gtctagctcc ttcctcgtgt tcggctccaa gaagctcaag   120
aatagcgcca attccatgct ggtcctgaag aaagactcga tcttcatgca gaagttctgc   180
tcctttcgca tcagtgcttc ggttgcgact gcctgc                             216

<210> SEQ ID NO 28
<211> LENGTH: 207
<212> TYPE: DNA
<213> ORGANISM: Artificial sequence
<220> FEATURE:
<223> OTHER INFORMATION: Description of Artificial Sequence:  Artificial
      primer

<400> SEQUENCE: 28
atggcggcac tggtgacctc ccagctcgcg acaagcggca ccgtcctgtc ggtgacggac    60
cgcttccggc gtcccggctt ccagggactg aggccacgga acccagccga tgccgctctc   120
gggatgagga cggtgggcgc gtccgcggct cccaagcaga gcaggaagcc acaccgtttc   180
gaccgccggt gcttgagcat ggtcgtc                                       207

<210> SEQ ID NO 29
<211> LENGTH: 433
<212> TYPE: DNA
<213> ORGANISM: Artificial
<220> FEATURE:
<223> OTHER INFORMATION: Description of Artificial Sequence:  Artificial
      primer

<400> SEQUENCE: 29
agatcttgag ccaatcaaag aggagtgatg tagacctaaa gcaataatgg agccatgacg    60
taagggctta cgcccatacg aaataattaa aggctgatgt gacctgtcgg tctctcagaa   120
cctttacttt ttatgtttgg cgtgtatttt taaatttcca cggcaatgac gatgtgaccc   180
aacgagatct tgagccaatc aaagaggagt gatgtagacc taaagcaata atggagccat   240
gacgtaaggg cttacgccca tacgaaataa ttaaaggctg atgtgacctg tcggtctctc   300
agaaccttta cttttatat ttggcgtgta ttttaaatt tccacggcaa tgacgatgtg   360
acctgtgcat ccgctttgcc tataaataag ttttagtttg tattgatcga cacggtcgag   420
aagacacggc cat                                                      433
```